(12) United States Patent
Park et al.

(10) Patent No.: US 11,004,673 B2
(45) Date of Patent: **\*May 11, 2021**

(54) HIGH-POWER ULTRAVIOLET (UV) AND VACUUM ULTRAVIOLET (VUV) LAMPS WITH MICRO-CAVITY PLASMA ARRAYS

(71) Applicant: Eden Park Illumination, Champaign, IL (US)

(72) Inventors: Sung-Jin Park, Champaign, IL (US); Cyrus M. Herring, Tolono, IL (US); James Gary Eden, Mahomet, IL (US)

(73) Assignee: Eden Park Illumination, Champaign, IL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/850,058

(22) Filed: Apr. 16, 2020

(65) Prior Publication Data
US 2020/0251324 A1    Aug. 6, 2020

Related U.S. Application Data

(63) Continuation of application No. 16/312,540, filed as application No. PCT/US2016/039488 on Jun. 27, 2016, now Pat. No. 10,658,170.

(51) Int. Cl.
*H01J 61/30*    (2006.01)
*A61L 2/10*    (2006.01)
(Continued)

(52) U.S. Cl.
CPC .............. *H01J 61/305* (2013.01); *A61L 2/10* (2013.01); *A61L 2/26* (2013.01); *C02F 1/325* (2013.01); *F02M 25/12* (2013.01); *H01J 9/248* (2013.01); *H01J 9/268* (2013.01); *H01J 9/39* (2013.01); *H01J 11/12* (2013.01); *H01J 11/18* (2013.01);
(Continued)

(58) Field of Classification Search
None
See application file for complete search history.

(56) References Cited

U.S. PATENT DOCUMENTS 6,762,556 B2   7/2004   Winsor
8,890,409 B2   11/2014  Eden et al.
(Continued)

FOREIGN PATENT DOCUMENTS

JP   2001281426 A   10/2001
JP   2010226053 A   10/2010
WO   2004032176 A1   4/2004

*Primary Examiner* — Dedei K Hammond
(74) *Attorney, Agent, or Firm* — Dickinson Wright PLLC

(57) ABSTRACT

A product having at least one plasma lamp that includes plates that are approximately parallel, with at least one array of microcavities formed in a surface of at least one plate. When desirable, the plates are separated a fixed distance by spacers with at least one spacer being placed near the plate's edge to form a hermetic seal therewith. A gas makes contact with the microcavity array. Electrodes capable of delivering a time-varying voltage are located such that the application of the time-varying voltage interacts with the gas to form a glow discharge plasma in the microcavities and the fixed volume between the plates. The glow discharge plasma efficiently and uniformly emits radiation that is predominantly in the UV/VUV spectral range with at least a portion of the radiation being emitted from the plasma lamp.

22 Claims, 16 Drawing Sheets

(51) Int. Cl.

| | | |
|---|---|---|
| C02F 1/32 | (2006.01) | |
| H01J 9/26 | (2006.01) | |
| H01J 61/16 | (2006.01) | |
| H01J 9/24 | (2006.01) | |
| H01J 11/12 | (2012.01) | |
| H01J 11/36 | (2012.01) | |
| H01J 65/04 | (2006.01) | |
| H01J 11/38 | (2012.01) | |
| H01J 11/18 | (2012.01) | |
| A61L 2/26 | (2006.01) | |
| F02M 25/12 | (2006.01) | |
| H01J 9/39 | (2006.01) | |
| H01J 61/02 | (2006.01) | |
| H01J 61/12 | (2006.01) | |
| H01J 61/42 | (2006.01) | |

(52) U.S. Cl.
CPC ............... *H01J 11/36* (2013.01); *H01J 11/38* (2013.01); *H01J 61/025* (2013.01); *H01J 61/125* (2013.01); *H01J 61/16* (2013.01); *H01J 61/42* (2013.01); *H01J 65/046* (2013.01); *A61L 2202/11* (2013.01); *A61L 2202/24* (2013.01); *A61L 2202/26* (2013.01); *C02F 2201/3228* (2013.01); *C02F 2303/04* (2013.01); *Y02W 10/37* (2015.05)

(56) References Cited

U.S. PATENT DOCUMENTS

| | | | |
|---|---|---|---|
| 8,900,027 | B2 | 12/2014 | Bulson et al. |
| 8,952,612 | B1 | 2/2015 | Pavliscak et al. |
| 2002/0036461 | A1 | 3/2002 | Schoenbach et al. |
| 2010/0072893 | A1 | 3/2010 | Eden et al. |
| 2010/0140511 | A1 | 6/2010 | Auday et al. |
| 2010/0253207 | A1 | 10/2010 | Joulaud et al. |
| 2010/0296978 | A1 | 11/2010 | Park et al. |
| 2012/0025696 | A1* | 2/2012 | Eden ............... H01J 29/20 313/486 |
| 2014/0265036 | A1* | 9/2014 | Eden ............... H01J 65/046 264/402 |

* cited by examiner

SEALING (FIRING) PROCESS

EVACUATION, GAS FILLING, FILL TUBE SEALING

HIGH-POWER ULTRAVIOLET (UV) AND VACUUM ULTRAVIOLET (VUV) LAMPS WITH MICRO-CAVITY PLASMA ARRAYS

CROSS REFERENCE TO RELATED APPLICATIONS

This application is a Continuation of U.S. patent application Ser. No. 16/312,540, filed on Dec. 21, 2018, which is a 35 U.S.C. § 371 national phase application of International Application Serial No. PCT/US2016/039488, filed Jun. 27, 2016, designating the United States and published in English, the entire contents of which are hereby incorporated herein by reference.

STATEMENT REGARDING FEDERALLY SPONSORED RESEARCH AND DEVELOPMENT

This invention was made with Government support under Award No. DE-SC0007698, awarded by the Small Business Innovative Research Program, U.S. Department of Energy. The Government has certain rights in this invention.

FIELD

This disclosure relates generally to plasma devices emitting radiation in the ultraviolet (UV) and vacuum ultraviolet (VUV) regions of the electromagnetic spectrum. More specifically, this disclosure relates to plasma lamps and products formed from plasma lamps, as well as a method of manufacturing the same.

BACKGROUND

The statements in this section merely provide background information related to the present disclosure and may not constitute prior art.

Ultraviolet (UV) and vacuum ultraviolet (VUV) radiation is generally defined to encompass the 200-400 nm and 100-200 nm wavelength regions, respectively, of the electromagnetic spectrum. Because the energies of VUV photons, for example, can be as large as approximately 12.5 eV, UV/VUV radiation is capable of initiating photochemical reactions that are inaccessible to optical sources emitting radiation of longer wavelengths and, therefore, lower photon energies. Since the strengths of many of the most important chemical bonds (e.g., C—H, O—H, etc.) are less than 10 eV, the commercial application of photochemical reactions hinges on the development of efficient and powerful sources of UV and VUV radiation.

Photochemical reactions that occur in the UV spectral region are responsible for many processes that have considerable medical and industrial value. Examples of such processes include the synthesis of Vitamin D and three-dimensional (3D) printing or stereolithography. Deep UV/VUV radiation is also effectively used to deactivate biological pathogens, disinfect water, clothing, and other surfaces, and desorb contaminants and hydrocarbons from otherwise clean surfaces, such as equipment devoted to semiconductor device fabrication. In addition, the use of UV radiation to disinfect a wound or surgical incision is believed to accelerate the healing process and hinder the occurrence of hospital-acquired infections.

Most applications that use UV/VUV radiation owe their existence to the development of incoherent optical sources that emit radiation at wavelengths lying between about 185 nm and 350 nm. Although lasers are presently available at several wavelengths that fall within this spectral region (e.g., $F_2$=157 nm; ArF=193 nm, KrCl=222 nm, KrF=248 nm, and XeCl=308 nm), these lasers offer little benefit in most industrial and medical applications due to their optical coherence, physically large size, cost (capital and operating), and inefficiency. For example, an argon fluoride (ArF) laser capable of producing 10 W of average power at 193 nm (100 mJ/pulse, operating at a pulse repetition frequency (PRF) of 100 Hz) is a formidable system. This type of laser is also quite large, expensive, heavy and, at a PRF of 100 Hz, requires maintenance after every few hundred hours of operation. In addition, the mean time between failure (MTBF) for commercial systems incorporating conventional lasers is generally limited by the laser itself. Therefore, although UV/VUV lasers have proven to be pivotal to several medical applications (such as the corneal refractive correction procedure known as LASIK, and the treatment of psoriasis), for example, lamps are the preferred solution for industrial applications if the requisite power and efficiency are available at the desired wavelength.

Despite the commercial potential of UV/VUV photochemistry, disinfection, and decontamination, the applications of 100-400 nm radiation have thus far been constrained by the generally low output powers available from conventional lamps. Because the optical power delivered by any UV/VUV lamp translates directly into the rate at which a photochemical or disinfection process proceeds, it is essential that lamps scalable to at least 1-10 W of average power be available in order for industrial and biomedical photochemical processes to reach their full potential. Indeed, the realization of high power, efficient lamps in the 100-400 nm wavelength region is expected to open the door to numerous commercial products and processes (requiring 3-12.5 eV photons) that were simply not accessible previously. Furthermore, it is desirable that the spectral breadth of the radiation emitted by such lamps be narrow (less than ~10 nm) because photochemical processes are renowned for their specificity. In other words, a photon of a given wavelength has a specific energy and, therefore, the absorption of a photon by an inorganic or biological molecule yields a product distribution that is also precisely defined. Expanding the spectral bandwidth to, for example, tens of nanometers negates the advantage associated with optically-driven chemical processes and will often result in adverse or competing effects. For example, the phototherapeutic treatment of psoriasis is known to be characterized by a narrow "action spectrum" centered at 308 nm. Irradiating human tissue with photons having wavelengths more than 1-2 nm from this spectral position may be harmful to the patient.

Unfortunately, few commercially-available UV/VUV lamps satisfy both expectations with regard to requirements for average power and spectral bandwidth. A high pressure Hg lamp, for example, is capable of emitting kilowatts of optical power but does so over a broad spectral range (typically 250-580 nm) that does not extend into the VUV region. In contrast, a low-pressure (or "resonance") Hg lamp emitting at 184.9 nm and 253.7 nm typically generates considerably less than tens of watts of average optical power. Furthermore, the deuterium ($D_2$) molecular lamp emits over a large spectral range and produces little power (<10 W). Another drawback of conventional UV/VUV lamps is their form factor. Generally available in the form of a cylinder, such lamps require expensive reflectors or other optics in order to maximize the efficiency for delivering the UV/VUV radiation to a surface, and for producing a spatially uniform distribution of intensity at that surface.

U.S. Pat. No. 8,900,027 describes a lamp that includes a first and second lamp substrate with a first and second external electrode, respectively, and a first and second internal phosphor coating, respectively. The first phosphor coating is a phosphor monolayer. The method of manufacturing a lamp includes screen-printing a phosphor monolayer on a first lamp substrate; screen-printing a phosphor layer on a second lamp substrate; joining the phosphor coated faces of the first and second lamp substrates together with a seal; and joining a first and second electrode to the uncoupled exterior faces of the first and second lamp substrates, respectively.

U.S. Pat. No. 6,762,556 describes an open chamber photoluminescent lamp. The photoluminescent planar lamp is gas-filled and contains photoluminescent materials that emit visible light when the gas emits ultraviolet energy in response to a plasma discharge. The lamp comprises first and second opposing plates manufactured from a glass material having a loss tangent 0.05%.

U.S. Publication No. 2002/036461 describes a discharge device for operation in a gas at a prescribed pressure that includes a cathode having a plurality of micro hollows therein, and an anode spaced from the cathode. Each of the micro hollows has dimensions selected to produce a micro hollow discharge at the prescribed pressure. Preferably, each of the micro hollows has a cross-sectional dimension that is on the order of the mean free path of electrons in the gas.

SUMMARY

The present disclosure generally provides a plasma lamp comprising, consisting of, or consisting essentially of two or more internal plates each having an interior surface and an exterior surface that are positioned approximately parallel to one another. At least one array of microcavities is formed in the interior surface of at least one of the internal plates. Optionally, one or more spacers may be located between the interior surfaces of the internal plates, such that the spacers maintain the separation between the internal plates at a predetermined distance. If the spacers are present, at least one spacer is a periphery spacer, placed near the edge of the internal plates so as to form a hermetic seal with the internal plates, thereby creating a fixed volume between the internal plates. A gas occupies the volume between the internal plates and is in contact with the array of microcavities. A plurality of electrodes is connected to a power supply designed to deliver a time-varying voltage. At least one electrode is located on the exterior surface of each internal plate. Optionally, one or more protective windows may be placed on the opposite side of at least one electrode in order to assist in providing environmental protection thereto. The time-varying voltage interacts with the gas, such that a spatially uniform, glow discharge (plasma) is formed both within the microcavities and the fixed volume between the internal plates (when spacers are present). The glow discharge (plasma) emits radiation that is in the UV/VUV spectral region, and the presence of microcavities improves (by at least a factor of two) the efficiency and output power of lamps having no microcavities but which are, in all other respects, identical to the microcavity-bearing lamp.

According to one aspect of the present disclosure, the microcavities exhibit at least one geometric shape. Each geometric shape exhibits a predetermined primary spatial width ($w_i$) that is in the range of about 3 µm to about 5,000 µm, and optionally, a spatial depth ($d_i$) that is in the range of about 1 µm to about 1,000 µm (1 mm). Alternatively, $d_i$ is between about 5 µm to about 600 µm, and $w_i$ is between about 5 µm to about 1,500 µm. The geometric shape of the microcavities may include, but are not limited to a hemisphere, a cylinder, a half-cylinder, an ellipsoid, a truncated cone, a paraboloid, a truncated ellipsoid, or a cube.

When desirable, at least two different arrays of microcavities can be located in the interior surface of at least one of the internal plates. The microcavities in the two (or more) arrays may exhibit a different geometric shape, different spatial dimensions, microcavity to microcavity spacing, or a combination thereof. The spatial dimensions may comprise one or more of depth ($d_i$) and width ($w_i$) as described above or further defined herein. The different arrays of microcavities can be spatially separated on the interior surface of the internal plate, or interlaced or interwoven, such that the microcavities in one array are alternated or staggered with respect to the microcavities of another array.

The plasma lamp according to one aspect of the present disclosure is planar and has a thickness that is about 6 mm or less. When desirable, the plasma lamp may comprise a curved surface. The plasma lamp exhibits an electrical efficiency of at least 1%; alternatively, greater than 10%; alternatively, between 1% and 10% with higher efficiencies (e.g., approaching 20%) being possible. One or more of the internal plates and protective windows in the plasma lamp are individually selected to comprise a UV/VUV radiation transmissive material. In addition, at least one of the plurality of electrodes exhibits a transparency to UV/VUV radiation of 90% or more, or the electrode geometry can be designed so as to have an "openness" or transmission above 90%. Each of the protective windows is individually selected to be a plate or a protective coating.

The gas may comprise one or more noble gases, one or more halogen gases, or a mixture of at least one halogen gas with the one or more noble gases. Depending on the desired radiation wavelengths, other gases or vapors (such as deuterium, Group-VI containing gases including hydrogen sulfide and sulfur hexafluoride, or water vapor) are also suitable candidates for producing UV/VUV radiation. When a plasma is formed in the gas, gases, or gas/vapor mixture, molecules and/or atoms are produced that emit UV/VUV radiation having a peak wavelength at which maximum intensity is generated. Examples of the molecules that can be produced, and their peak wavelengths, include, without limitation, NeF* (108 nm), $Ar_2$* (126 nm), $Kr_2$* (146 nm), $F_2$* (157 nm), ArBr* (165 nm), $Xe_2$* (172 nm), ArCl* (175 nm), KrI* (190 nm), ArF* (193 nm), KrBr* (207 nm), KrCl* (222 nm), KrF* (248 nm), XeI* (254 nm), $Cl_2$* (258 nm), XeBr* (282 nm), $Br_2$* (289 nm), ArD* (290-300 nm), XeCl* (308 nm), $I_2$* (342 nm), or XeF* (351, 353 nm). When the gas is xenon and the UV/VUV radiation emitted from the $Xe_2$* excimer molecule has a peak wavelength of about 172 nm, the average output intensity of the plasma lamp can be greater than 200 mW per $cm^2$ of lamp surface area, and the peak power generated by lamps of the present disclosure can be greater than 1 kW.

The spacers, when present, can be either part of a monolithic structure that exhibits a predetermined spacer pattern or discrete structures having the shape of a disc, a sphere, a pellet, a cylinder, a cube, or the like, as well as a mixture thereof. The spacers keep the plates separated at a predetermined fixed distance and serve to maintain the relative position of the two inner plates so that they are substantially parallel to one another.

When desirable, the plasma lamp may further comprise a planar or curved reflector or a reflecting surface, positioned at the rear surface of the lamp, so as to increase the total UV/VUV radiation produced out of the front of the lamp.

The reflector can be integrated with, or affixed to, the plasma lamp. The plasma lamp may also comprise a UV/VUV conversion phosphor layer located on the interior surface of at least one internal plate, serving to convert the UV/VUV spectrum naturally emitted by a specific gas/vapor combination to another wavelength, or range of wavelengths, better suited to a specific industrial application or process.

According to another aspect of the present disclosure, a product may be realized that comprises the plasma lamp of the present disclosure and produces UV/VUV radiation for use in a predefined application. The predefined application may include, without limitation, disinfecting potable water; disinfecting medical devices or clothing; deactivating biological pathogens; treating waste water; desorbing contaminants or hydrocarbons from a surface of a chamber or other component or system used in a cleanroom environment; generating ozone near the air intake of an internal combustion engine; curing a coating composition after it has been applied to a surface of a substrate; or photolyzing a single gas or vapor, or a mixture of gases and vapors, so as to yield a gaseous or solid product that is otherwise difficult to produce efficiently or inexpensively. When desirable, a commercial product may comprise a plurality of plasma lamps. The plurality of plasma lamps can be tiled in order to exhibit an emitting surface that produces an average power between (for example) 100 W and 10 kW in the UV/VUV spectral range. Optionally, the product can produce radiation simultaneously in two or more wavelength ranges within the UV/VUV spectral region.

According to yet another aspect of the present disclosure, a method of forming a plasma lamp having a composite structure is provided. This method generally comprises providing two or more internal plates. Each of the internal plates has an interior surface and an exterior surface. At least one microcavity array is formed in the interior surface of at least one of the internal plates. The interior surface of each internal plate is positioned such that it faces the interior surface of another internal plate. Optionally, one or more spacers may be located between the inner surfaces of the internal plates, such that the spacers keep the internal plates separated by a predetermined fixed distance. When present, at least one spacer is a periphery spacer placed near the edge of the internal plates so as to form a hermetic seal between the periphery seal and the internal plates, thereby creating a fixed volume between the internal plates. A gas fill port is then formed that passes through at least one of the internal plates and the cavity is filled with a gas or mixture of gases capable of producing a glow discharge plasma. The gas is also in contact with the array of microcavities. The gas fill port is then closed in order to seal the gas within the plasma lamp.

A plurality of electrodes is formed with at least one electrode being located on the exterior surface of each internal plate. The plurality of electrodes is connected to a power supply designed to deliver a time-varying voltage. Optionally, one or more protective windows may be formed over at least one electrode; alternatively over each electrode.

The time-varying voltage is applied to the electrodes such that a spatially uniform, glow discharge plasma is formed within one or more of the microcavity arrays and in the volume between the internal plates (if present). The glow discharge plasma emits radiation that is in the UV/VUV spectral region.

When desirable, forming the microcavity array comprises applying a mask having a desired microcavity array pattern to an interior surface of an internal plate using, without limitation, a stamping or replica molding process or a lithographic process. Subsequently, the microcavity array is formed in the interior surface of the internal plate using a micropowder ablation process, a laser ablation process, a drilling process, a chemical etching process, or the like-processes that are well-known to artisans in the field.

The method further comprises applying a glass frit to both surfaces of the spacers that make contact with the inner surface of the interior plates. The glass frit is designed for use in a firing process, such that a hermetic seal between the spacer and the interior surfaces of the internal plates is accomplished. Before closing the gas fill port, the method may further include operating the plasma lamp, evacuating the gas from the void volume, and refilling the void volume with a fresh amount of the gas. Optionally, the method may also comprise placing a getter within the plasma lamp in order to remove residual impurities. The lamp may also be heated in an oven during the gas evacuation/refill process so as to clean ("de-gas") the lamp interior more quickly and thoroughly.

Further areas of applicability will become apparent from the description provided herein. It should be understood that the description and specific examples are intended for purposes of illustration only, and are not intended to limit the scope of the present disclosure.

BRIEF DESCRIPTION OF THE DRAWINGS

The drawings described herein are for illustration purposes only and are not intended to limit the scope of the present disclosure in any way.

FIGS. 6 (C, D) is a plan (top) view of another array design for a plasma lamp, showing tow interlaced arrays having microcavities of a single cross-sectional shape in two sizes;

DETAILED DESCRIPTION

Figure 1A:
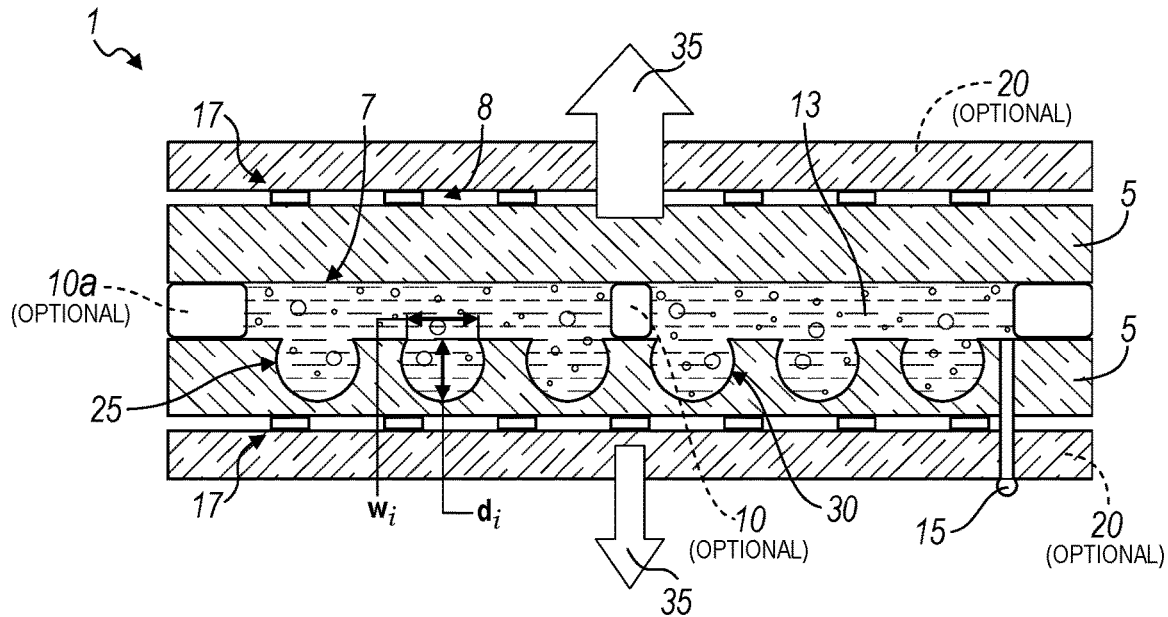
FIG. 1A is a cross-sectional schematic representation of a plasma lamp formed according to the teachings of the present disclosure.

The following description is merely exemplary in nature and is in no way intended to limit the present disclosure or its applications. For example, the plasma lamps made and used according to the teachings contained herein are described throughout the present disclosure as being flat or planar in geometry in order to more fully illustrate the lamps and the use thereof. However, the formation of a plasma lamp comprising the various features and elements defined herein that incorporates or utilizes a different form factor, such as one that includes a curved surface, is also contemplated to be within the scope of the present disclosure. It should be understood that throughout the description, corresponding reference numerals indicate like or corresponding parts and features.

The present disclosure generally provides plasma lamps that are able to generate watts of average power at discrete wavelengths within the ultraviolet (UV) and vacuum ultraviolet (VUV) spectral ranges, extending from approximately 100 nanometers to about 400 nanometers. For example, an output intensity above about 200 mW/cm$^2$ can be achieved reproducibly and continuously from a plasma lamp that emits at 172 nm (hv=7.2 eV; Xe$_2$* is the emitter). This level of intensity corresponds to an average power of more than 20 W delivered from a 100 cm$^2$ (4"×4") lamp that is generally flat and thin (e.g., ≤6 mm in thickness). In addition, the peak power produced by this 172 nm plasma lamp is currently above 1 kW which is attractive for photochemical applications requiring the simultaneous absorption of two or more photons by an atom or molecule. Furthermore, the volumes of lamps formed according to the teachings of the present disclosure are typically 3-4 orders of magnitude smaller than a laser of the same average output power. Therefore, the lamps described here are more powerful and efficient than virtually all of the lasers that have been developed since 1963 in the VUV spectral region, for example.

Figure 10:
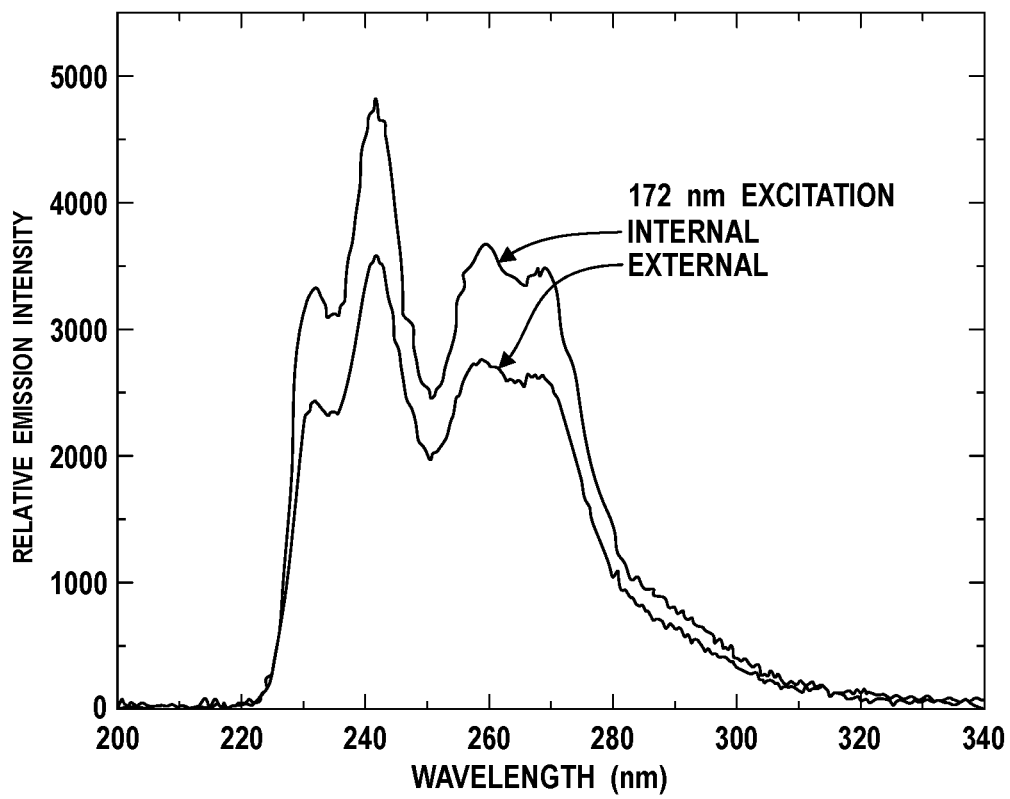
FIG. 10 is a graphical representation of the spectrum produced by a VUV-to-UV conversion phosphor film, driven by xenon dimer emission at 172 nm and coated onto an interior surface of a lamp of the present disclosure.

Referring to FIGS. 1A and 10, the plasma lamp 1 generally comprises, consists of, or consists essentially of two or more internal plates 5 with each internal plate 5 having an interior surface 7 and an exterior surface 8 that is arranged so that the internal surface 7 of each plate 5 is substantially parallel to one another. At least one of the plates 5 should be highly transmissive at the wavelengths of the desired emission from the lamp. At least one array 25 of microcavities 30 is formed in the interior surface 7 of at least one of the internal plates 5. Optionally, one or more spacers 10 may be located between the interior surfaces 7 of the internal plates 5, such that the spacers 10 keep the internal plates 5 separated at a predetermined fixed distance. When present, at least one spacer 10 is a periphery spacer 10a that is placed near the edge of the internal plates 5. The periphery spacer 10a forms a hermetic seal with the internal plates 5 and creates a fixed volume of space between the internal plates 5. A gas 13, in which a glow discharge (plasma) is produced, occupies this volume of space. Thus, the gas 13 is also in contact with the array 25 of microcavities 30. When desirable, the plasma lamp 1 may be formed with no spacers being present between the interior surfaces 7. In this type of design, the plasma discharge is formed within the array of microcavities 30.

A plurality of electrodes 17 is connected to a power supply 18 that is designed to deliver a time-varying voltage. At least one electrode 17 is located on the exterior surface 8 of each of the internal plates 5. Finally, one or more protective windows 20 may optionally be placed on the opposite side of each electrode 17 in order to provide further environmental protection thereto. Such windows are not essential for the operation of lamps of the present disclosure and, in fact, absorb a fraction of the UV/VUV emission generated within the lamp. A portion of the lamp emission absorbed by the lamp windows is the result of color centers produced in the window material by the high intensities characteristic of lamps of the present disclosure.

When the time-varying voltage interacts with the gas 13, a spatially uniform glow discharge (plasma) is formed both within the microcavities 30 and the fixed volume between the internal plates 5. It is this glow discharge plasma that emits the desired radiation 35 in the UV/VUV spectral region. It must be emphasized that the streamers characteristic of conventional dielectric barrier discharge lamps are absent or strongly suppressed by lamps of the present disclosure. This characteristic alone allows for these UV/VUV lamps to operate at higher gas pressures (thereby generating larger output powers) while maintaining a spatially-homogeneous discharge within the lamp. The microcavity arrays fabricated within the lamp not only produce a uniform glow discharge but also stabilize the lamp, resulting in the production of short (less than 100 ns) pulses of radiation that are essentially identical for each cycle of the driving voltage waveform.

Conventional lamps that are in the shape of a bulb or cylinder generally require the presence of optics to counteract the focusing of the UV/VUV radiation by the lamp envelope itself (which can behave as a lens). In addition, capturing the radiation that exits a conventional lamp in directions other than that desired for the intended application requires collimating optics for this spectral region that are often expensive and fragile. In comparison, the plasma lamps of the present disclosure eliminate the expense of mating a cylindrical UV/VUV lamp with reflective or transmissive collimating or focusing optics. Plasma lamps that are flat and thin may also be tiled so as to realize emitting surfaces of several square meters in area (or more) that produce average powers exceeding 100-1000 W in the UV/VUV spectral region. Such power levels are unprecedented for lamps that are compact in size and emit radiation in a narrow band. This same statement also generally holds true for lasers that operate in the VUV region. In fact, only two VUV lasers—namely, ArF and $F_2$—are normally capable of generating Watts of average power. However, neither of these lasers can be regarded as being either compact or inexpensive. Furthermore, the duty cycle of high power UV/VUV lasers is typically on the order of $10^{(-6)}$ for a PRF of 100 Hz, whereas lamps of the present disclosure have already been operated at PRF values up to 135 kHz which corresponds to a duty cycle above 0.1%, or more than three orders of magnitude higher than that of most UV/VUV lasers.

The substantial increase in power measured for the plasma lamps formed according to the teachings of the present disclosure, relative to the power measured for conventional lamps, occurs due to several factors. One of these is the presence of at least one array of microcavities in the lamp. The microcavities serve the purpose of locally shaping the electric field strength in the plasma that is responsible for producing the desired UV/UVV radiation. Thus, the microcavities intensify the local electric field which has the result of more effectively producing the electronically-excited atoms and molecules essential to producing the desired UV/VUV radiation.

Still referring to FIG. 1A, microcavities 30 that comprise one or more geometries are fabricated into an interior surface 7 of at least one of the internal plates 5 or windows of the lamp 1 through which the radiation produced by the lamp passes. The shape of the micro-cavities may include, but not be limited to, a hemisphere, a cylinder, a half-cylinder, an ellipsoid, a truncated cone, a paraboloid, a truncated ellipsoid, and a cube. The microcavities 30 may exhibit different spatial dimensions, center-to-center spacing (known as the pitch), or a combination thereof. The spatial dimensions may include one or more of depth ($d_i$) and width ($w_i$).

The microcavities 30 also provide the ability to enhance the efficiency of the lamp. These microcavities 30 are effective at producing spatially-uniform glow discharges within the lamp, even at gas pressures 13 at which conventional lamp technology generates only streamers that are distributed statistically (in both space and time), within the lamp 1. Other functions of the array 25 of microcavities 30, such as the improved utilization of the voltage pulse powering the system, also provide various benefits. In the absence of the array 25 of microcavities 30 in the plasma lamp 1, the output power is measured to fall precipitously (by a factor of at least four in the case of a lamp 1 that emits radiation at a peak wavelength of about 172 nm). According to one aspect of the present disclosure, at least one array 25 of microcavities 30 is fabricated into a surface 7 of a plate 5 or window that is internal to the lamp 1, and oriented such that the plane in which the array resides is approximately parallel to another internal plate 5 or window of the lamp 1. Other aspects of the present disclosure do not require that the two internal surfaces of the lamp be parallel.

Figure 1B:
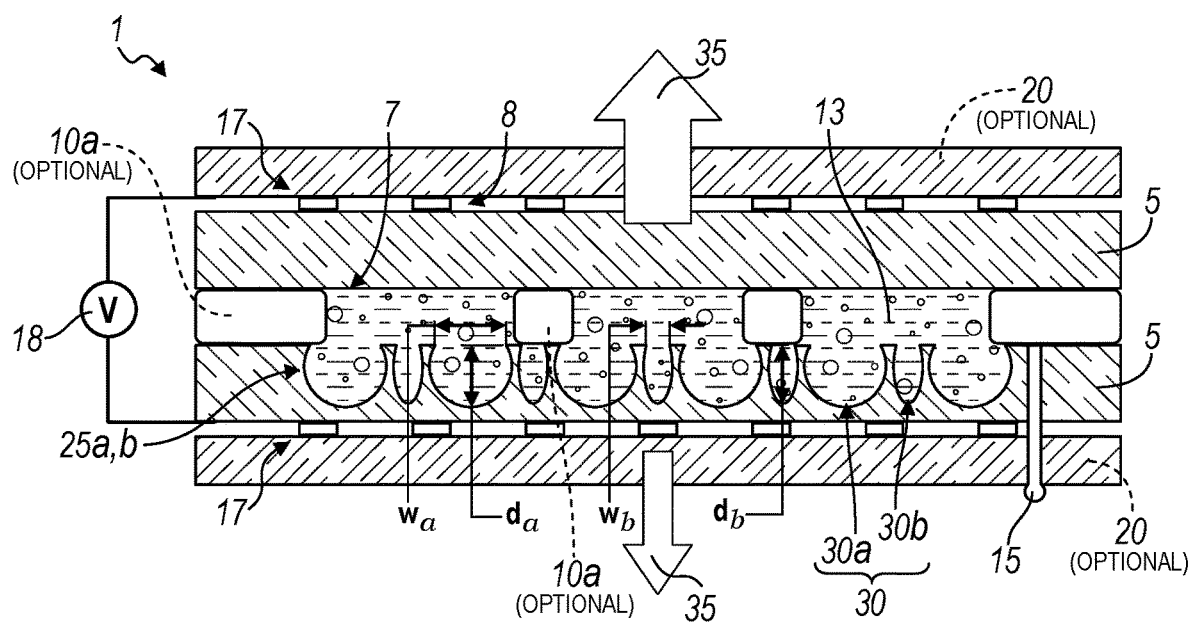
FIG. 1B is a cross-sectional schematic representation of another aspect of a plasma lamp of the present disclosure.

Referring now to FIG. 1B, at least two arrays 25a, 25b of microcavities 30a, 30b are fabricated into at least one internal surface 5 of the plasma lamp 1. The second array 25b is chosen to have microcavities 30b with geometries and/or spatial dimensions that are different from those of the microcavities 30a constituting the first array 25a. As shown in the specific example of FIG. 1B, the shape of the microcavities 30a in the first array 25a is hemispherical with a primary spatial dimension ($w_a$), while the shape of the microcavities 30b in the second array 25b is elliptical with a primary spatial dimension ($w_b$), wherein $w_b < w_a$. The function of the second array 25b of microcavities 30b is to form a plasma within each microcavity 30b at a threshold breakdown voltage level (BVL) that is different from the threshold BVL of the microcavities 30a in the first array 25a. When desirable, the different arrays 25a, 25b of microcavities 30a, 30b may be spatially separated on the interior surface 7 of the internal plate 5, or interlaced or interwoven, such that the microcavities 30a in one array 25a are alternated or staggered with the microcavities 30b of another array 25b.

One advantage associated with the design of the plasma lamp in the present disclosure is that the voltage waveform driving the lamp is utilized more effectively and efficiently by the light-generating plasma, as compared to a lamp having internally a single array of micro-cavities, all of which are of the same geometry and spaced by the same pitch. If chosen properly, interlaced arrays of microcavities are able to substantially enhance the efficiency of UV/VUV lamp emission because the "power pulse" (I×V, where I and V represent the time-varying current and voltage waveforms, respectively) that drives the lamp is more effectively utilized. That is, smaller diameter microcavities in one array, for example, will ignite (have plasma produced within them) at voltages higher than those required for larger microcavities (presuming the same gas and a constant pressure). Thus, having microcavities of more than a single size and geometry is advantageous with respect to utilization of the driving electrical waveform and, therefore, the efficiency of the lamp. In tests conducted over the past two years, this conclusion has been confirmed by studies of multiple lamps, half of which did not have microcavities. Care was taken in the fabrication of the lamps without microcavities to ensure that the improvement in lamp efficiency for the microcavity-bearing lamps was not the result of thinning one or both of the internal plates 5. That is, the depth of the microcavities decreases, in effect, the thickness of the plates and so several lamps without microcavities were fabricated with an internal plate 5 thickness that compensated for this effect. The data consistently showed a factor of at least two (and, often, a factor of more than four) increase in the output power of lamps having microcavity arrays, relative to lamps that did not incorporate microcavity arrays. Furthermore, dual cavity array lamps are more efficient than single array lamps.

The planar plasma lamps of the present disclosure are capable of emitting at multiple discrete wavelengths in the UV and VUV spectral regions, and do so with unprecedented levels of intensity. For example, a flat lamp that emits radiation at 172 nm (photon energy of 7.2 eV) in the VUV spectral range through a single quartz internal plate or window can generate intensities ≥200 mW/cm². Intensities above 240 mW per square cm of lamp surface area have been realized with considerably higher values possible upon optimization of the microcavity array structure, the gas mixture, and the spacer thickness. Although the design of a planar plasma lamp favors emission through a single internal plate or window, an emission intensity above 140 mW/cm² may also be emitted through a second internal plate or window. Therefore, a 100 cm² (4"×4") plasma lamp can generate more than 20 W of average power through the single internal window alone. Such large power levels have not been available previously nor has the flat form factor, and thickness, of lamps of the present disclosure been known previously. Existing, commercially-available 172 nm lamps, for example, generally emit a maximum intensity of 50 mW/cm² VUV radiation which is at least a factor of four smaller than intensities achieved with lamps of the present disclosure. As described above, removing the array(s) of microcavities from lamps of the present disclosure (e.g., the rest of the lamp structure otherwise remains the same) reduces the output intensity of the modified plasma lamps typically by at least a factor of two or three.

The gas may comprise one or more noble gases, one or more halogen gases, or a mixture of at least one halogen gas with the one or more noble gases. The gas, when desired, may include other gases or vapors, such as one or more metal-halides, sodium, mercury, or sulfur, to name a few. Alternatively, the gas may comprise neon (Ne), xenon (Xe), or a mixture thereof with the ratio of Ne-to-Xe (Ne:Xe) ranging between 1:99 to 99:1; alternatively, 25:75 to 75:25; alternatively, between 40:60 to 60:40; alternatively, about 50:50. The pressure for the gas contained within the plasma lamp can range from about 100 Torr to well over one atmosphere; alternatively, between 100 Torr and 760 Torr; alternatively, one atmosphere or more. Lamps designed to efficiently produce radiation from the Ar dimer at 126 nm, for example, are expected to have internal gas pressures of at least several bar (atmospheres).

When a plasma is produced within the microcavities, molecules are formed in electronic states that emit UV/VUV radiation having a peak wavelength (i.e., the wavelength corresponding to maximum intensity). Molecules of particular interest, and their associated peak wavelengths, include, without limitation, NeF* (108 nm), Are* (126 nm), $Kr_2$* (146 nm), $F_2$* (158 nm), ArBr* (165 nm), $Xe_2$* (172 nm), ArCl* (175 nm), KrI* (190 nm), ArF* (193 nm), KrBr* (207 nm), KrCl* (222 nm), KrF* (248 nm), XeI* (254 nm), $Cl_2$* (258 nm), XeBr* (282 nm), $Br_2$* (289 nm), ArD* (290-300 nm), XeCl* (308 nm), $I_2$* (342 nm), or XeF* (351, 353 nm). When the gas is xenon and the UV/VUV radiation emitted from the $Xe_2$* excimer molecule is at a peak wavelength of about 172 nm, the average output intensity of the plasma lamp can be greater than 200 mW/cm² and the peak power can be greater than 1 kW.

Referring again to FIGS. 1A-1C, the main body of the plasma lamp 1 comprises two interior flat plates 5 that are optionally separated by spacers 10. If the wavelength(s) of the light to be generated by the lamp is beyond approximately 300 nm, the plates can be fabricated from a relatively inexpensive glass, such as borosilicate glasses. However, if (as shown in FIG. 1B), the lamp is intended to produce radiation in the deep-UV or VUV (wavelength λ<300 nm), then the two inner plates can be fabricated from fused silica or quartz. Preferably, the fused silica (or quartz) is of high quality in that it exhibits low absorption at the emission wavelength(s). A primary cause of absorption by window materials (such as fused silica or quartz) in the UV and VUV spectral regions is the formation of color centers. Alternatively, sapphire may serve in this capacity, although sapphire is birefringent and generally expensive. Into at least one of the two internal plates 5 is fabricated an array 25 of microcavities 30, each having a spatial depth ($d_i$) and width ($w_i$).

The spacers that are sometimes used to separate the internal plates a fixed distance and to maintain the plates parallel to one another may be, without limitation, either part of a monolithic structure that exhibits a predetermined spacer pattern or discrete structures having the shape of a disc, a sphere, a pellet, a cylinder, a cube, or the like, as well as a combination thereof. The distance between the internal surfaces of the internal plates is predetermined by the size of the spacers utilized. The separation distance between the plates is between about 0 mm (when no spacers are used) to about 2.0 mm, but can alternatively be larger or smaller; alternatively, between about 0.6 and 1.0 mm. The spacer positions are retained by any suitable mechanism, including but not limited to, the use of friction between the surface of the spacer and internal plate or by bonding through the use of a phosphor coating or other material, such as a frit.

The depth ($d_i$) of the microcavities generally range from about 1 micrometer to 1,000 micrometers (µm); alternatively between about 5 µm and about 600 µm; alternatively, from about 10 µm to about 600 µm. The spatial width ($w_i$) of the microcavities range from about 3 µm to about 5,000 µm; alternatively between about 5 µm and about 1,500 µm, alternatively, from about 25 µm to about 500 µm. When at least two arrays 25a, 25b of microcavities are fabricated into the lower of the two flat plates as shown in FIG. 1B, the two arrays can be distinguishable in that the microcavities in each array may exhibit different shapes, as well as depth ($d_a$, $d_b$) and/or spatial width ($w_a$, $w_b$) dimensions.

The breakdown voltage associated with a gas may scale with the product of the gas pressure (p) and the primary dimensions ($d_i$, $w_i$) of the microcavities. Therefore, for a fixed value of gas pressure, plasma will be produced in microcavities, having different dimensional values, at different values of the driving voltage. In effect, microcavities of differing dimensions will ignite (generate plasma) at different values of voltage imposed across the lamp.

Figure 1C:
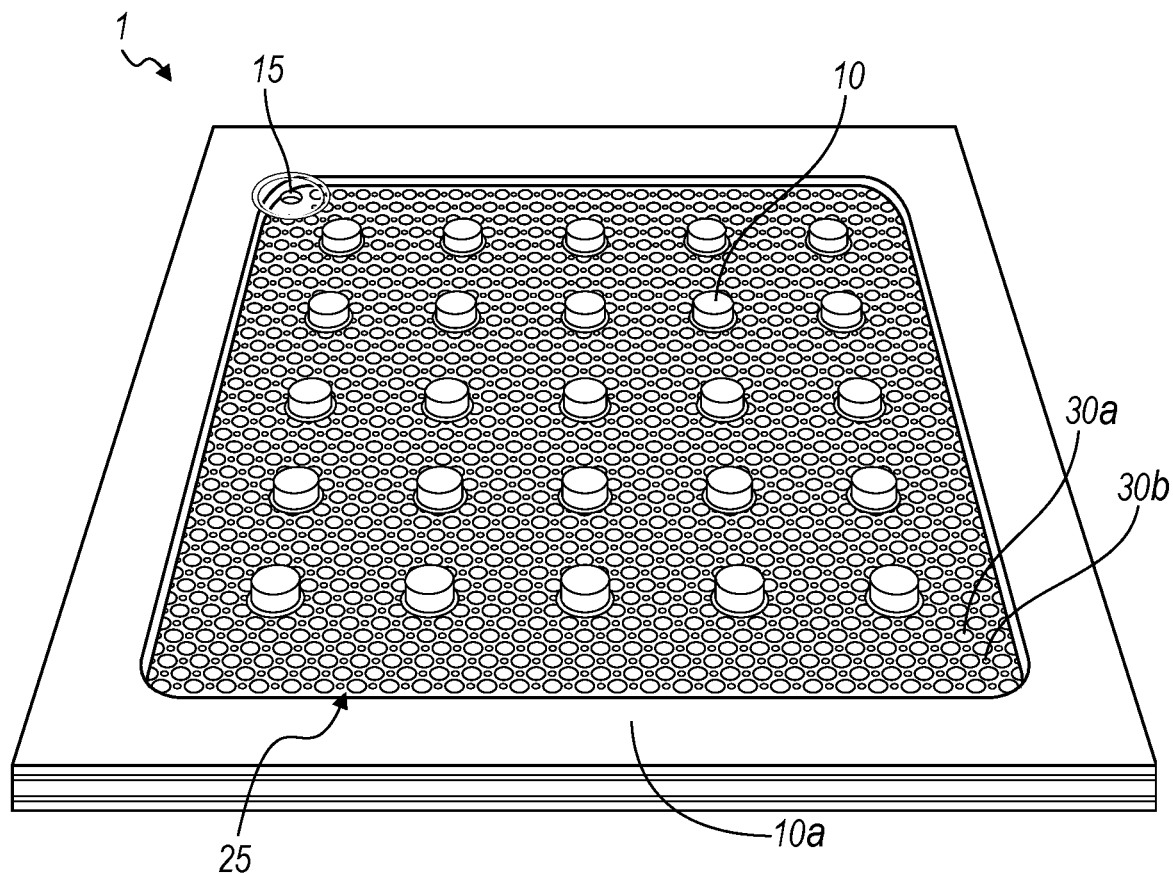
FIG. 1C is a top-down perspective view of the plasma lamp of FIG. 1B.

Still referring to FIGS. 1A-1C, electrical power is applied to the plasma lamp 1 by means of electrodes 17 applied to the outer surface 8 of the two inner plates 5. The electrodes 17 can take on one of many forms, such as a grid of narrow nickel films (lines) deposited onto the outer surface 8 of the plate 5 by evaporation, sputtering, or any other deposition process known in the art. Several specific examples of materials that may be used as electrodes include, but are not limited to, transparent conductive oxides (TCO) such as indium tin oxide (ITO), fluorine-doped tin oxide (FTO), or doped zinc oxide, among others; films comprising carbon nanotubes, graphene, or the like; transparent conducting polymers, such as poly(3, 4-ethylenedioxythiophene) [PEDOT], doped PEDOT, poly(4, 4-dioctylcyclo-pentadithiophene), or derivatives of polyacetylene, polyaniline, polypyrrole or polythiophene; or a patterned metal or metal alloy, such as copper, gold, nickel, or platinum, to name a few.

The transparency through the electrode should be above 85%; alternatively, above 90% and, preferably, between 90% and about 97%. In the case of patterned metal lines, overall transparency ("openness") is calculated by comparing the lamp surface area occupied by the electrodes lines, as compared to the total emitting area of the lamp. The lamp 1 assembly is completed by attaching two additional windows 20 to the exterior of the lamp 1 that cover the electrodes 17. These external windows 20 are provided as a safety precaution, but also serve the purpose of protecting the electrodes 17 from exposure to the environment.

As further indicated in FIGS. 1A-1C, a through-channel or gas fill port 15 (e.g., a circular hole) is also provided in one of the internal plates 5, as well as its associated outer window 20, in order to permit the evacuation of air originally present within the fixed volume enclosed by the plates 5 and spacers 10 in the lamp 1, as well as backfilling of the lamp 1 with the desired gas(es) or vapors 13. Alternatively, the gas fill port is positioned through an internal plate that contains a microcavity array.

Since the structure of the plasma lamp is that of a dielectric barrier discharge (DBD) device, the driving voltage should be time-varying. Specific examples of two voltage waveforms include, but are not limited to, a 20 kHz sinusoid and bipolar pulses that have a rise time of <100 nanoseconds (ns) and an adjustable PRF. When assembled, the plasma lamp has an overall thickness of typically about 6 mm or less.

When the internal plate 5 and the external window 20 of the plasma lamp are made of a radiation transmissive material, UV/VUV radiation may be transmitted through the plate and window to the environment. For example, UV/VUV radiation may emerge from the plasma lamp through both faces of the lamp when all of the plates and windows are made of a transmissive material. Most of the optical radiation is emitted through the front face of the lamp (i.e., through the plate/window that is opposite to the window containing the array of microcavities). However, for lamps tested to date, the intensity of the radiation emitted through the opposite or rear face of the lamp can be as much as 70% of that exiting the lamp through the front face. Accordingly, this lamp technology is well-suited for use in applications that require double-sided emission.

When emission of UV/VUV radiation through a single face of the lamp is desired, a simple planar reflector can be affixed to the rear face of the lamp (e.g., behind the array of microcavities, on the exterior face of the inner plate or either face of the outer plate). The planar reflector can be integrated with or affixed to the plasma lamp. The intensity of the UV/VUV radiation that is emitted through the front face of the plasma lamp may increase by 40% or more when a reflecting surface is added to the rear face of the lamp. The planar reflector may comprise a diffractive structure such that a preferred wavelength or wavelengths is reflected preferentially by the reflector.

Figure 2A:
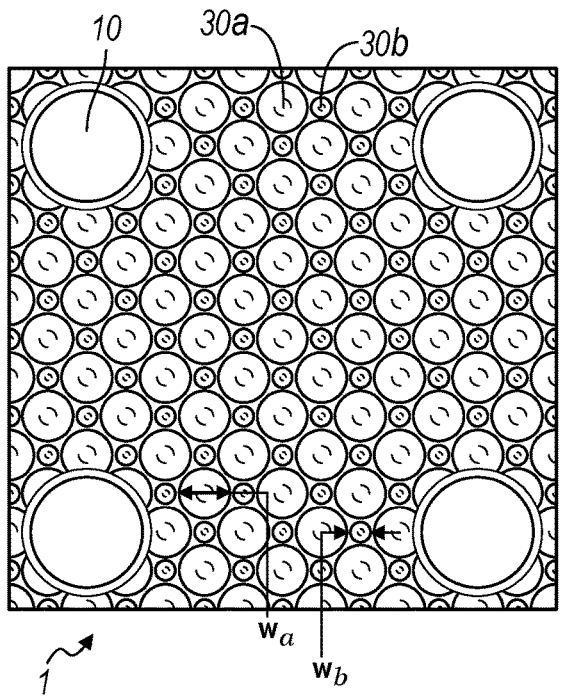
FIG. 2A is an image of the emission generated by the plasma lamp of FIGS. 1B-10 when the lamp is driven with a sinusoidal AC voltage waveform.
Figure 2B:
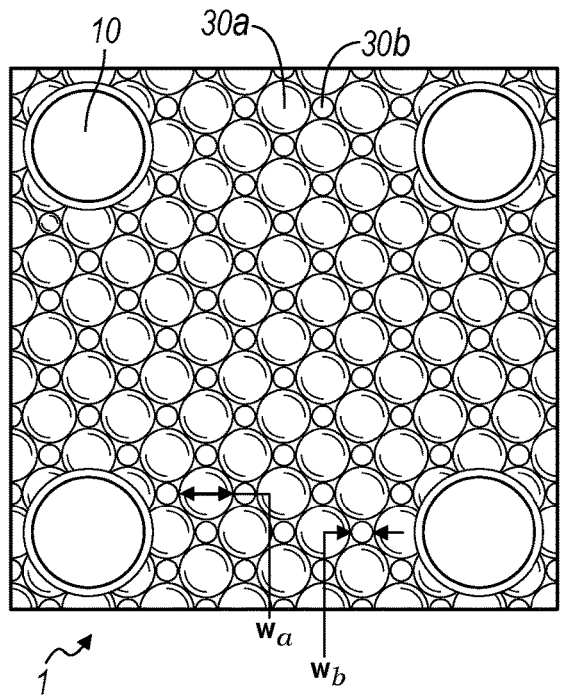
FIG. 2B is an image of the emission from the plasma lamp of FIGS. 1B-1C when the lamp is driven with a fast rise time, pulsed voltage waveform.

Referring now to FIGS. 2A and 2B, a photomicrograph of an assembled 5"×5" plasma lamp 1 (surface area of approximately 156 square cm) constructed with fused silica internal plates and external windows according to the schematic of FIG. 1B is shown during operation. These images provide a clear view of the microcavity pattern present in the lamp, and demonstrate the impact of the driving voltage waveform on the plasma distribution in and around the microcavities. Both FIGS. 2A and 2B are micrographs of a portion of the lamp 1 surface, recorded with a telescope and a CCD camera during operation of the lamp. The lamp is operated with xenon (Xe) gas filled to a pressure of 450 Torr and, because the emitter of interest in this case ($Xe_2$*) produces radiation in the VUV spectral region at 172 nm, a small amount of oxygen was intentionally introduced to the Xe gas in the lamp so that visible (green) fluorescent light emitted from the xenon monoxide (XeO) molecule allows for the visual assessment of lamp performance. More specifically, fluorescence emitted by the XeO* molecule allows for the visualization of the two different-sized hemispherical microcavities 30a, 30b that are present in the arrays of the lamp 1. In this image, the larger circles in the photomicrograph are the fused silica spacers 10 used to separate the internal plates.

In FIG. 2A, a 20 Hz (1.7 $kV_{RMS}$) sinusoidal ac waveform is utilized as the driving voltage to uniformly produce light emission throughout the larger microcavities 30A in one array. Although all of the microcavities in the plasma lamp 1 are hemispherical in shape, the width ($w_a$) of the larger hemispheres 30a is ~2 mm whereas the diameter of the smaller hemispheres 30b, which are situated at the intersection of four larger hemispheres, is ~800 µm.

In FIG. 2B, the distribution of fluorescence emanating from the microcavities 30a, 30b is strongly altered when a 30 kHz (1.4 $kV_{peak}$) waveform, comprising pulses with a rise time of less than 100 ns (~1 µs in duration), is utilized as the driving voltage for the lamp. In this case, the emission is more clearly confined to the microcavities and the increased electric field strength generated by the pulses, combined with the parabolic transverse profile of each microcavity, intensifies emission from the center of the hemispheres. As expected, the performance of plasma lamp 1 is dependent upon the spatial distribution and geometry of the arrays of microcavities present within the lamp.

Figure 3:
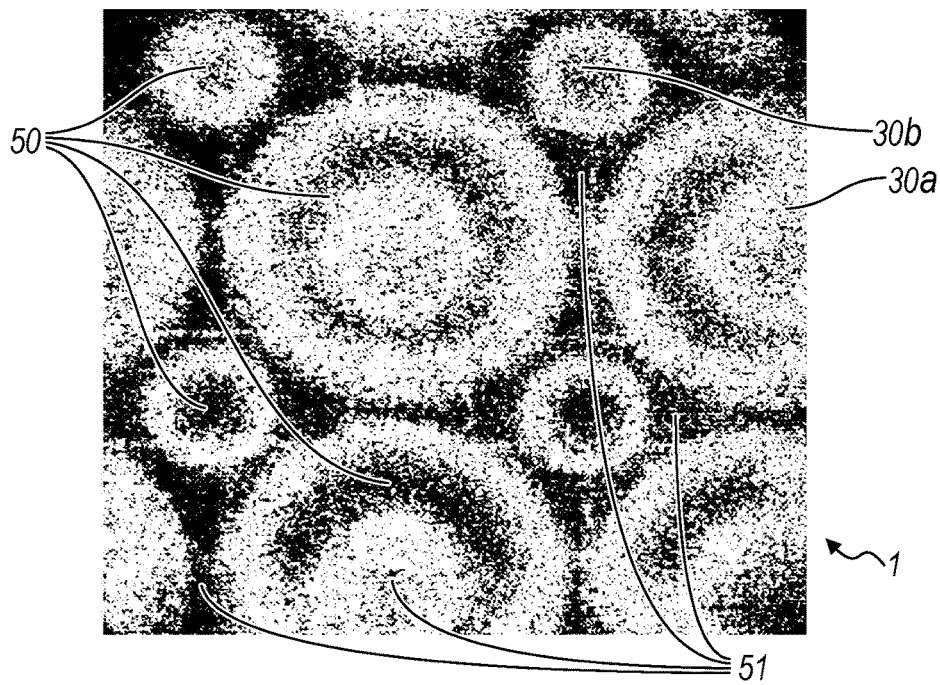
FIG. 3 is an optical micrograph of the emission generated by a portion of two interlaced microcavity arrays in the plasma lamp of FIGS. 1B-1C.

A gated, intensified CCD camera can be used to observe the temporal behavior of the arrays. Referring now to FIG. 3, a false color image is provided in which areas 50 that are red in color represent the greatest radiation intensities observed, whereas areas 51 that are blue denote the lowest observed emission intensities. The image shows a small portion of two interlaced arrays (for a 100 $cm^2$ (4"×4") lamp) in which the diameters of the hemispheres for the two arrays are 2 mm and 800 µm, as described above with respect to FIGS. 2A and 2B. The gas mixture introduced to this lamp 1 is 315 Torr of Xe and 135 Torr of Ne. The lamp is powered by the application of a 20 kHz (1.8 $kV_{RMS}$) ac sinusoidal voltage. For this particular microcavity array design, emission from the larger hemisphere microcavities 30a takes on the form of an annulus, whereas the smaller hemisphere micro-cavities 30b produce emission in a more spatially-uniform manner. Time-resolved measurements of the fluorescence with a gated, intensified CCD camera, demonstrates that the larger cavities 30a ignite first as the driving voltage is rising whereas the smaller cavities 30b ignite later. Thus, cavities of different size interact with, and absorb power from, different portions of the driving voltage waveform. This behavior is partially responsible for the high electrical efficiency of these lamps which is presently 13%, but is expected to reach at least 20% in the future.

Figure 4:
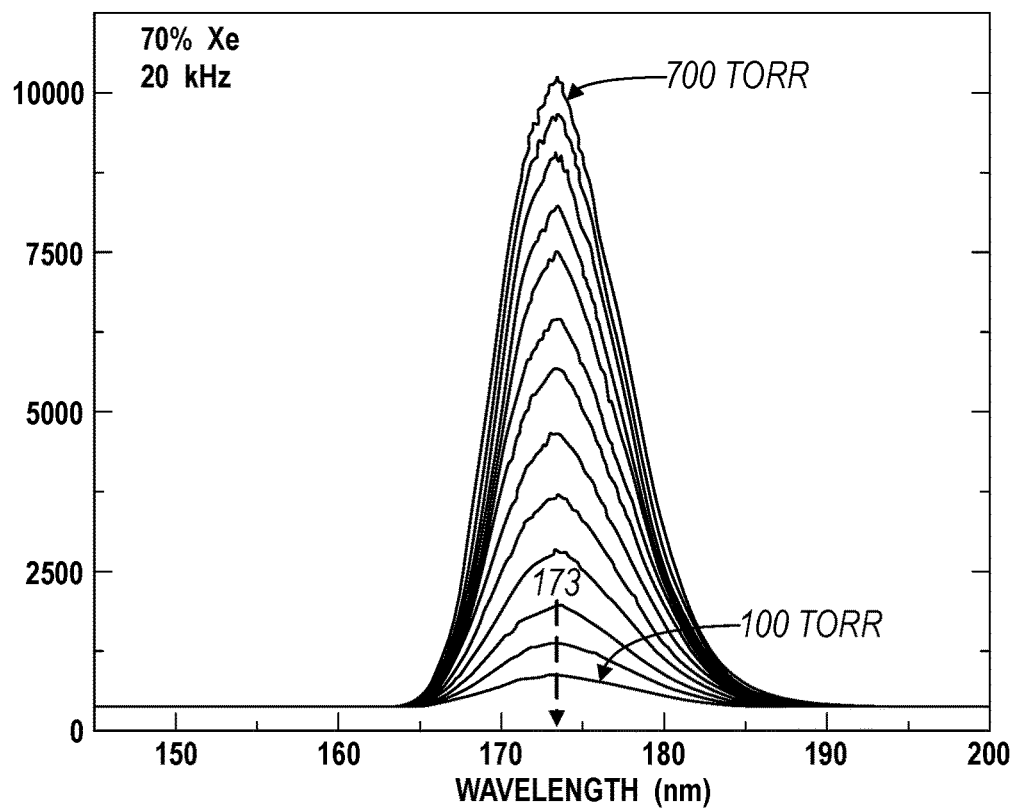
FIG. 4 is a graphical representation of the VUV spectrum (intensity as a function of wavelength) produced by a lamp of the present disclosure having a Ne/Xe gas mixture.
Figure 5:
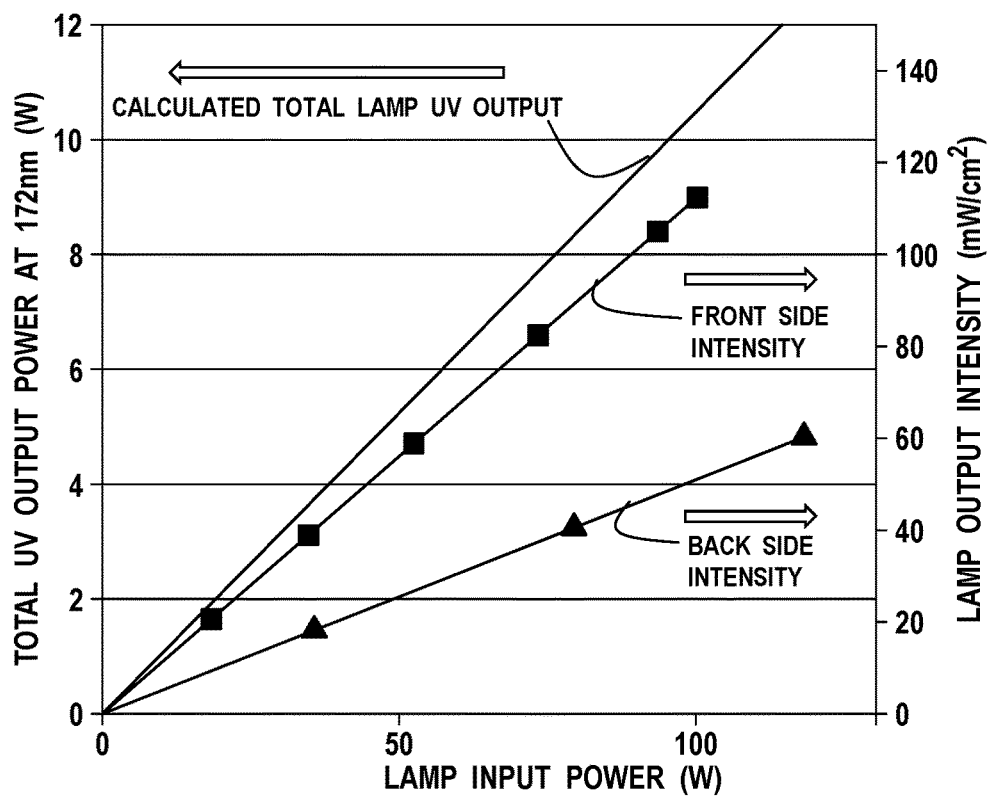
FIG. 5 is a graphical representation of the total VUV output power, and output intensity, plotted as a function of the input electrical power, for a plasma lamp fabricated according to the teachings of the present disclosure.
Figure 6A:
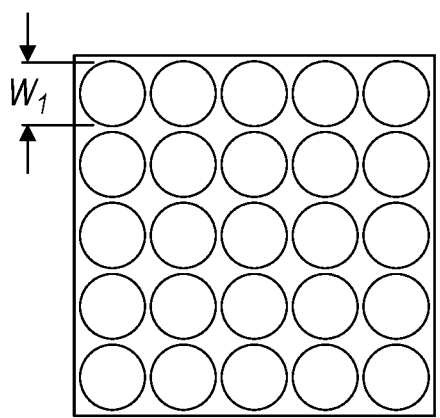
FIGS. 6 (A, B) is a plan (top) view of one design of a microcavity array having microcavities of one size and shape.
FIG. 6E is a plan (top) view of another microcavity array design for a plasma lamp, illustrating interlaced arrays with micro-cavities having two distinct shapes in three sizes.
Figure 6B:
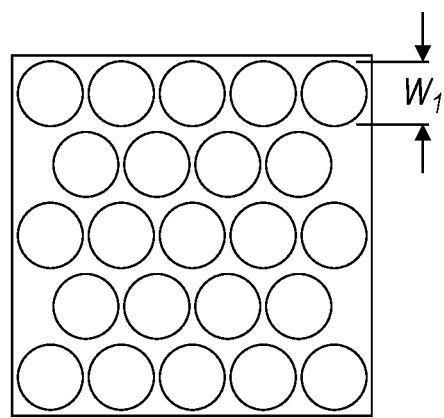
Figure 6C:
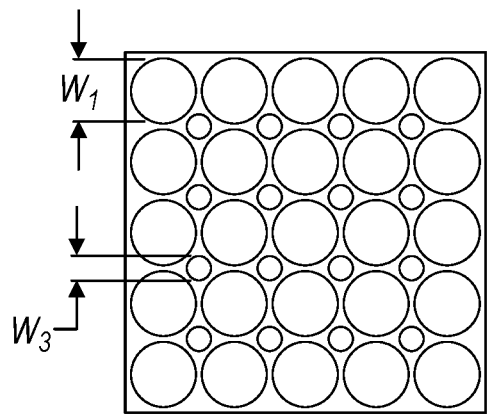
Figure 6D:
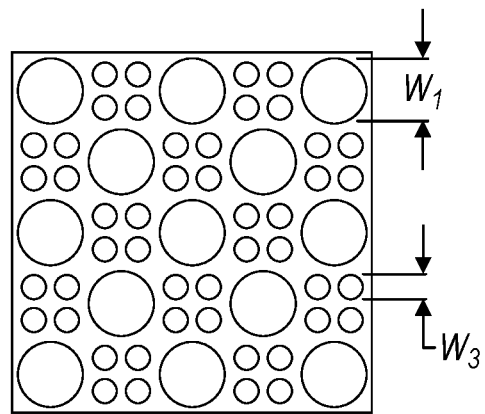
Figure 6E:
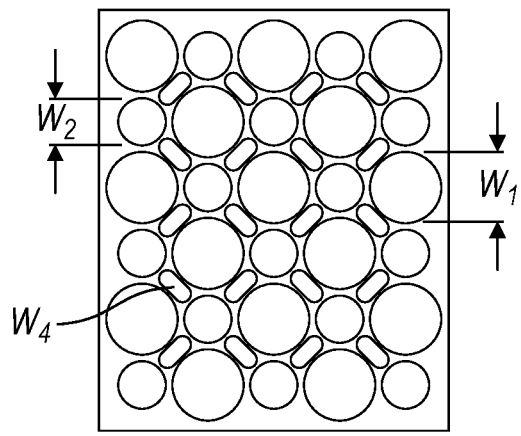

Referring now to FIG. 4, a spectrum representative of a 70/30% Xe/Ne gas mixture is shown for a plasma lamp having two interlaced arrays of microcavities. The emitted radiation of the $Xe_2$* excimer molecule is measured using a VUV spectrometer and a photomultiplier. Peak emission occurs near 172 nm and the wavelength-integrated emission grows rapidly with the partial pressure of the xenon gas. The spectral width of the $Xe_2$* radiation is ~9 nm. Measurements of the intensity of the $Xe_2$* emission generated by a 100 $cm^2$ (4"×4") lamp clearly show that microcavity-based lamps are capable of efficiencies, and values of total radiated power, that have not been previously attainable. For example, measurement of the intensity and power radiated by a 100 $cm^2$ $Xe_2$* lamp is summarized in FIG. 5. For a xenon (Xe) gas pressure in the lamp of 500 Torr, intensities above 200 $mW/cm^2$ are radiated by the lamp when the input power to the lamp is 160 W. This maximum value of intensity corresponds to more than 20 W of power (at 173 nm) that is radiated through both faces of the lamp, and the overall efficiency (VUV output power divided by the electrical power delivered to the lamp) is >10%.

Lamps identical in size and shape to that of FIG. 2, except having no arrays of microcavities, show a reduction in the maximum intensity and its output power to ~70 mW/cm$^2$ and 9 W, respectively. Furthermore, without microcavities in the plasma lamp, the plasma consists entirely of striations ("filaments") and, thus, the spatial homogeneity of the plasma is poor. In comparison, the incorporation of one or more arrays of microcavities results in the plasma becoming a diffuse glow with the VUV output radiation being spatially uniform over the entire surface of the lamp.

Referring now to FIGS. 6A-6E, several possible designs (among many) for plasma lamps having one, two, or more interlaced arrays of microcavities are shown, without limitation, in which the range of geometries and sizes of the microcavities are varied. If the primary array comprises cylindrical, truncated cone, or paraboloidal cavities with an exit aperture (i.e., the aperture facing the output window) of $w_1$, then the utilization of the surface occupied by the array, as well as the electrical utilization of the driving voltage waveform, is enhanced by the introduction of a second or third array of microcavities.

Figure 7A:
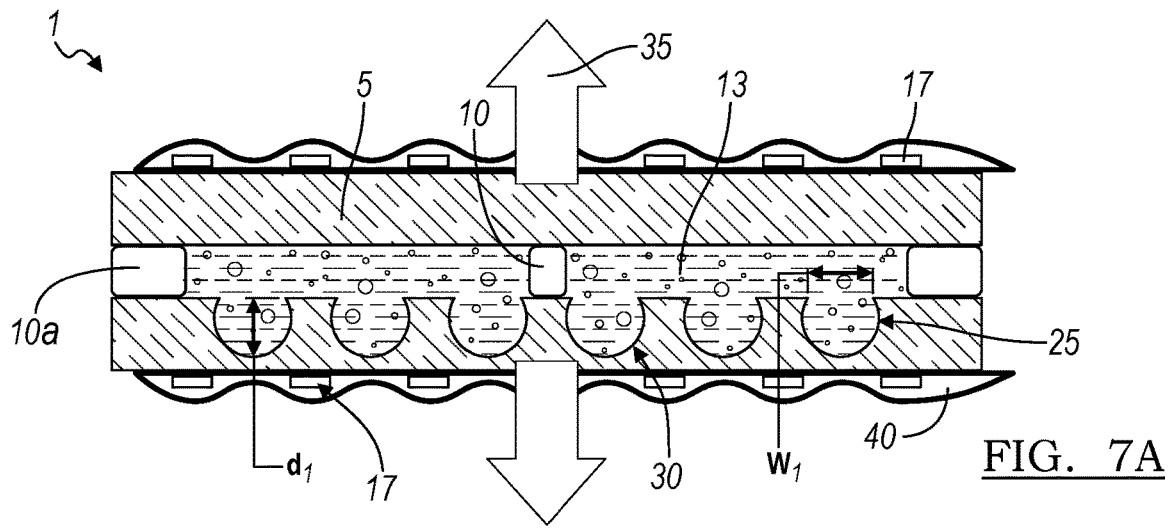
FIG. 7A is a cross-sectional schematic representation of a plasma lamp having a dual-sided, staggered microcavity array.

Referring now to FIG. 7A, a plasma lamp 1 having a simplified structure is shown in which the outermost windows 20 in FIG. 1A have been removed. In this situation, the deposition of a thin film 40 of an UV/VUV transmissive material onto the electrodes 17 is desirable to provide for limited environmental protection. This transmissive material 40 may be, but is not limited to, an aluminum oxide or diamond film.

Figure 7B:
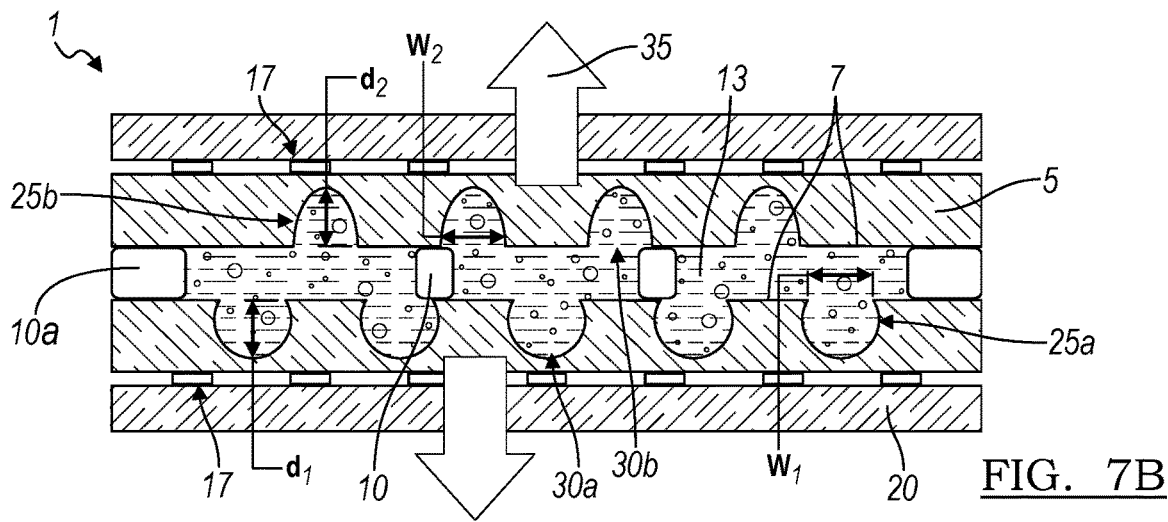
FIG. 7B is a cross-sectional schematic representation of a plasma lamp having an external electrode with a protective coating.

Referring now to FIG. 7B, an alternative structure for a plasma lamp 1 is shown in which two arrays 25a, 25b of the microcavities 30a, 30b are fabricated such that one array 25a, 25b is provided in the interior faces 7 of both of the inner fused silica plates 5. The microcavities 30a, 30b can be similar or different in shape and size. In FIG. 7B, the first array 25a comprises microcavities 30a having a depth $d_1$ and width $w_1$, while the second array 25b comprises microcavities 30b having a depth $d_2$ and width $w_2$. By staggering or interlacing the positions of the microcavities 30a, 30b on the interior face 7 of each plate 5, the efficiency of the UV/VUV radiation that can be emitted from the lamp 1 can be enhanced.

Figure 7C:
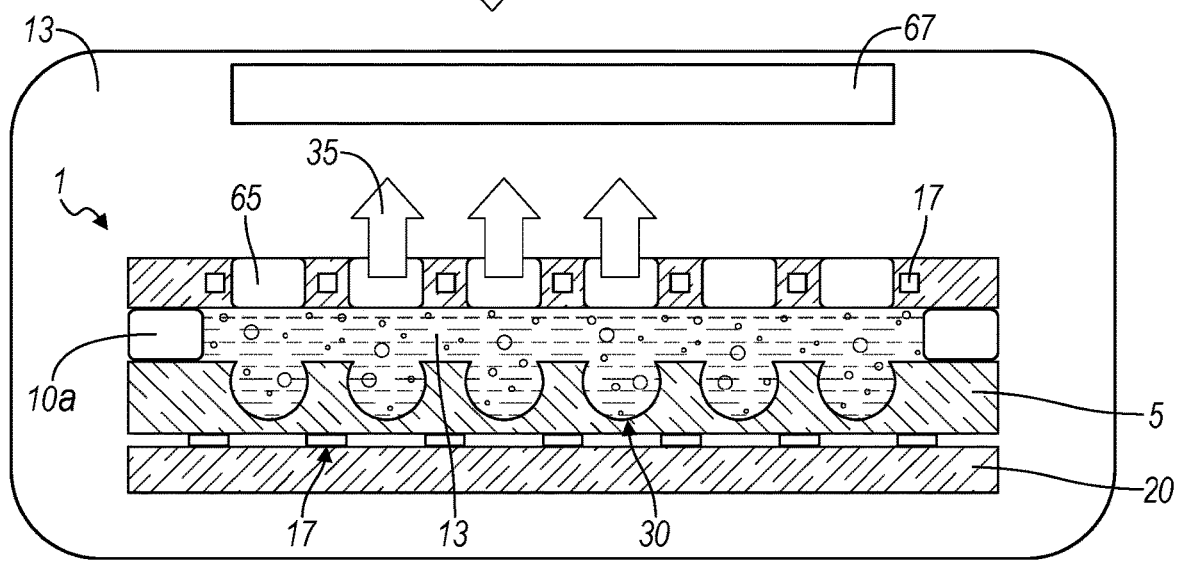
FIG. 7C is a cross-sectional schematic representation of a plasma lamp located within a chamber filled with at least one discharge gas.

The last example structure shown in FIG. 7C is one in which the inner plate 5 and outer window 20 on one side of the lamp have been removed to provide an open space or open window 65 structure. The primary function of this structure is to avoid the absorption of lamp radiation 35 by the internal plate 5 and external plate/window 20. This issue is of increasing importance as the wavelengths(s) of the radiation 35 produced by the lamp is decreased and approaches the LiF "cutoff" wavelength of approximately 106 nm. Emission from diatomic molecules such as H$_2$ and Ne$_2$ lie at wavelengths at which virtually all window materials absorb (e.g., deep into the vacuum ultraviolet, $\lambda$<120 nm) and, as illustrated in FIG. 7C, immersing the "target" 67 and intervening region between the target and the lamp with the same gas 13 or gas mixture within the lamp 1 is one approach to avoiding the loss of lamp power caused by window absorption.

Figure 8A:
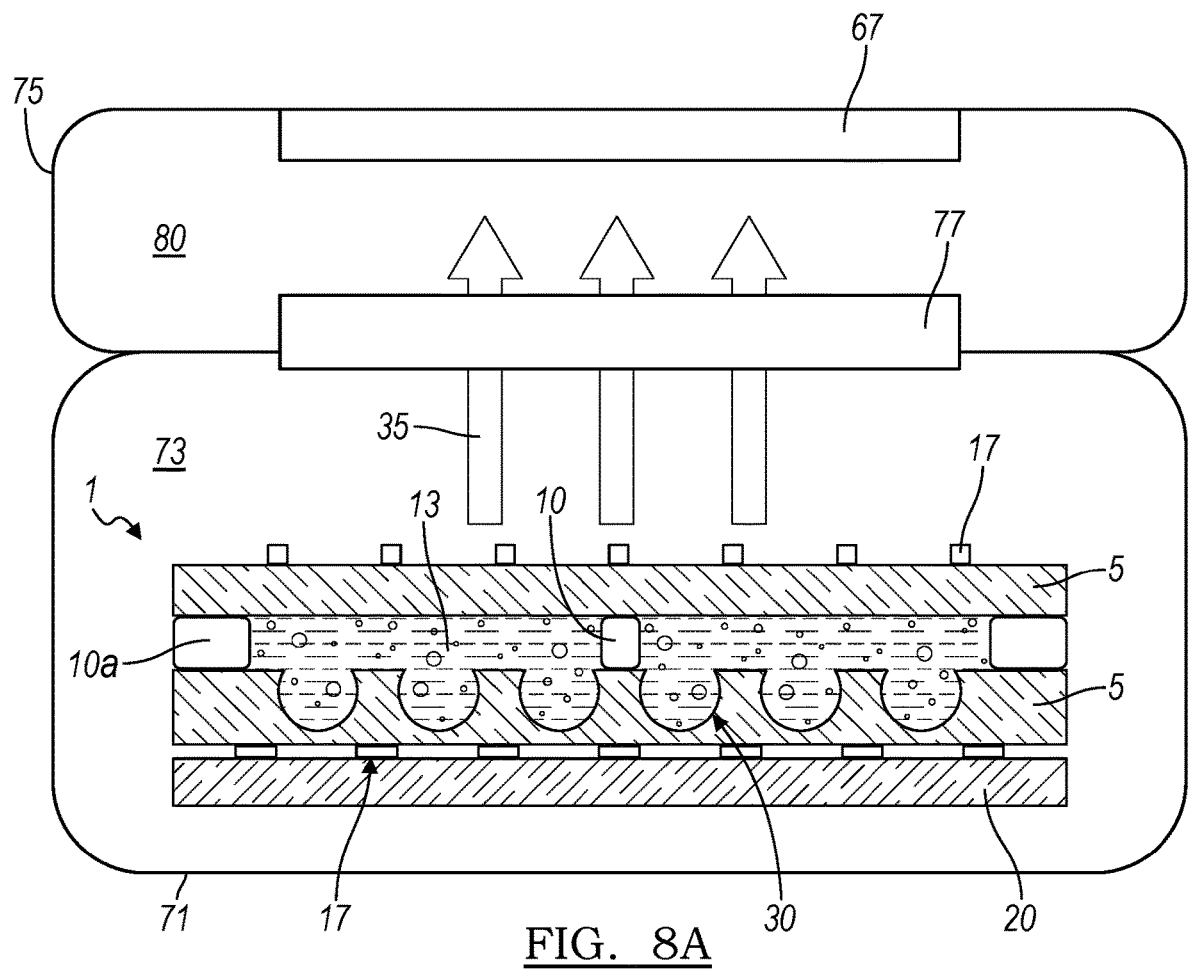
FIG. 8A is a cross-sectional, schematic representation of the plasma lamp of FIG. 7C, further including a secondary gas chamber.
Figure 8B:
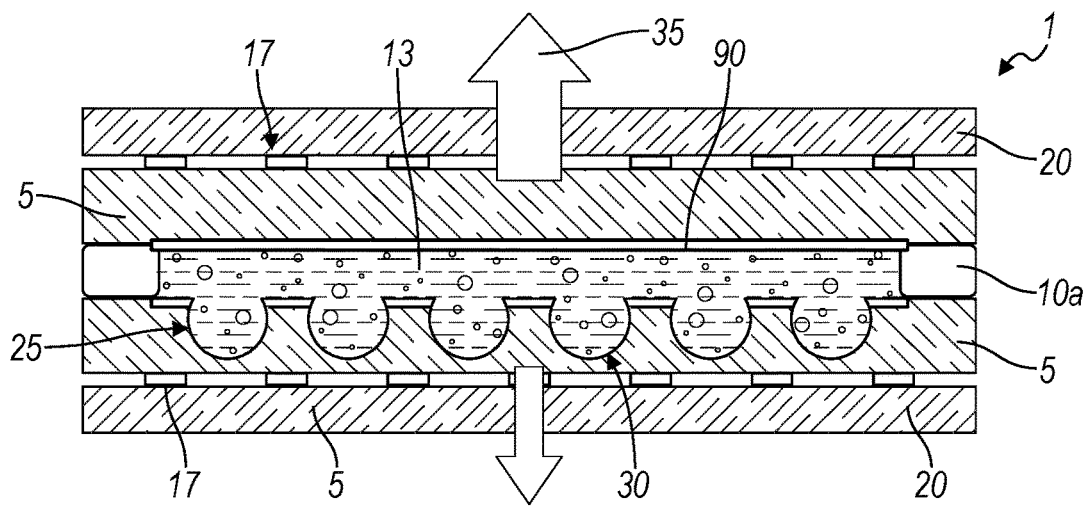
FIG. 8B is a cross-sectional schematic representation of a plasma lamp comprising a UV conversion phosphor.

FIGS. 8A and 8B illustrate, without limitation, two other specific design possibilities associated with the plasma lamps formed according to the teachings of the present disclosure. One of these designs (FIG. 8A) isolates a plasma lamp 1 from a secondary chamber 75 with a window 77 capable of efficiently transmitting the lamp radiation. The secondary chamber 75 may contain a gas 80 or vapor (or mixtures thereof) different than the gas 13 present within the plasma lamp 1. Gas or vapor 80 is selected so that, when irradiated by radiation 35 from the plasma lamp 1, a film will grow on the "target" 67 which could be, for example, a substrate or chip for an electronic circuit. In order to reduce absorption loss of the emitted radiation 35 from the plasma lamp 1, the lamp may be placed into a chamber 71 that can be evacuated to produce a vacuum 73. A specific example would be a 172 nm lamp irradiating a mixture of ammonia (NH$_3$) and trimethylgallium ((CH$_3$)$_3$Ga) so as to yield a thin film of gallium nitride (GaN) on the substrate.

Referring now to FIG. 8B, alternatively, a plasma lamp 1 can be designed such that it is well-suited for the photochemical production of various molecules of commercial interest. One example is that of formic acid and, in this situation, provision is made for the extraction of the photochemical product from the gas phase. The diagram illustrates a lamp 1 in which UV/VUV radiation 35 produced by the gas/gas mixture 13 within the lamp 1 is converted to other wavelengths by a phosphor material 90 or mixture of phosphor materials deposited onto the interior faces 7 of the inner plates 5. The phosphor material or mixture of phosphor materials may cover the entire interior surface 7 of the internal plates 5, or it can be stenciled or patterned such that the phosphor covers only a portion of the surface 7 of the internal plates 5. The composition of the phosphor materials may include, but not be limited to, oxides, nitrides, oxynitrides, sulfides, selenides, halides, or silicates of zinc, cadmium, manganese, aluminum, silicon, various rare earth metals, or a mixture thereof. The phosphor material may be applied as a single layer or as multiple layers with the composition of each layer being individually controlled. The thickness of the phosphor layers may range from about 0.5 µm to about 100 µm; alternatively, it can be between about 8 µm to about 25 µm. The phosphor layers may be applied by any means, including screen printing, spraying, curtain coating, dip coating, sputtering, or chemical vapor deposition.

Figure 9:
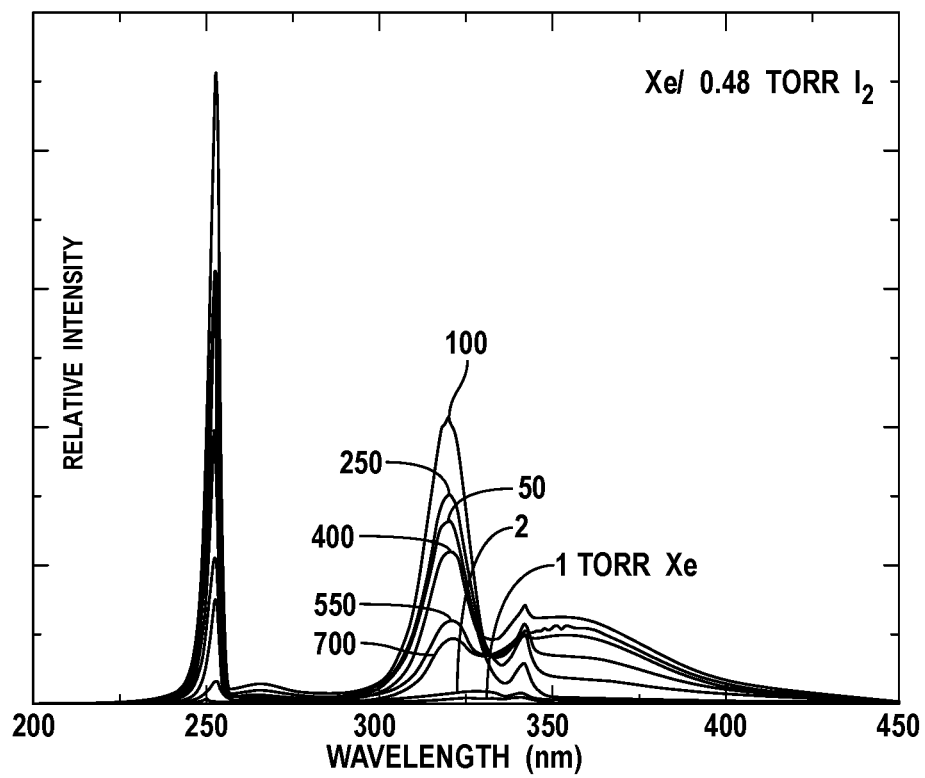
FIG. 9 is a graphical representation of the spectrum of the XeI (xenon monoiodide) excimer generated by a lamp formed according to the teachings of the present disclosure.

The plasma lamps of the present disclosure are capable of emitting UV/VUV radiation in the wavelength range of about 100 nm to 400 nm; alternatively between about 126 nm to about 353 nm. In FIG. 9, representative spectra (lamp intensity plotted as a function of wavelength) are provided for a plasma lamp having a mixture of Xe gas and iodine (I$_2$) vapor. The most intense feature in this spectrum is the B→X emission band of xenon monoiodide (XeI*), which peaks at 254 nm.

FIG. 10 shows the emission spectrum measured for the plasma lamp of FIG. 9 when the lamp is filled with xenon (Xe) gas, and the internal surface of one interior plate is coated with a film of a phosphor material. In this case, the 172 nm emission from the Xe$_2$* molecule is "down-converted" to the 230-290 nm spectral region. The second trace in this spectrum is that recorded when the phosphor material is coated onto the outer face(s) of the lamp.

Figure 11:
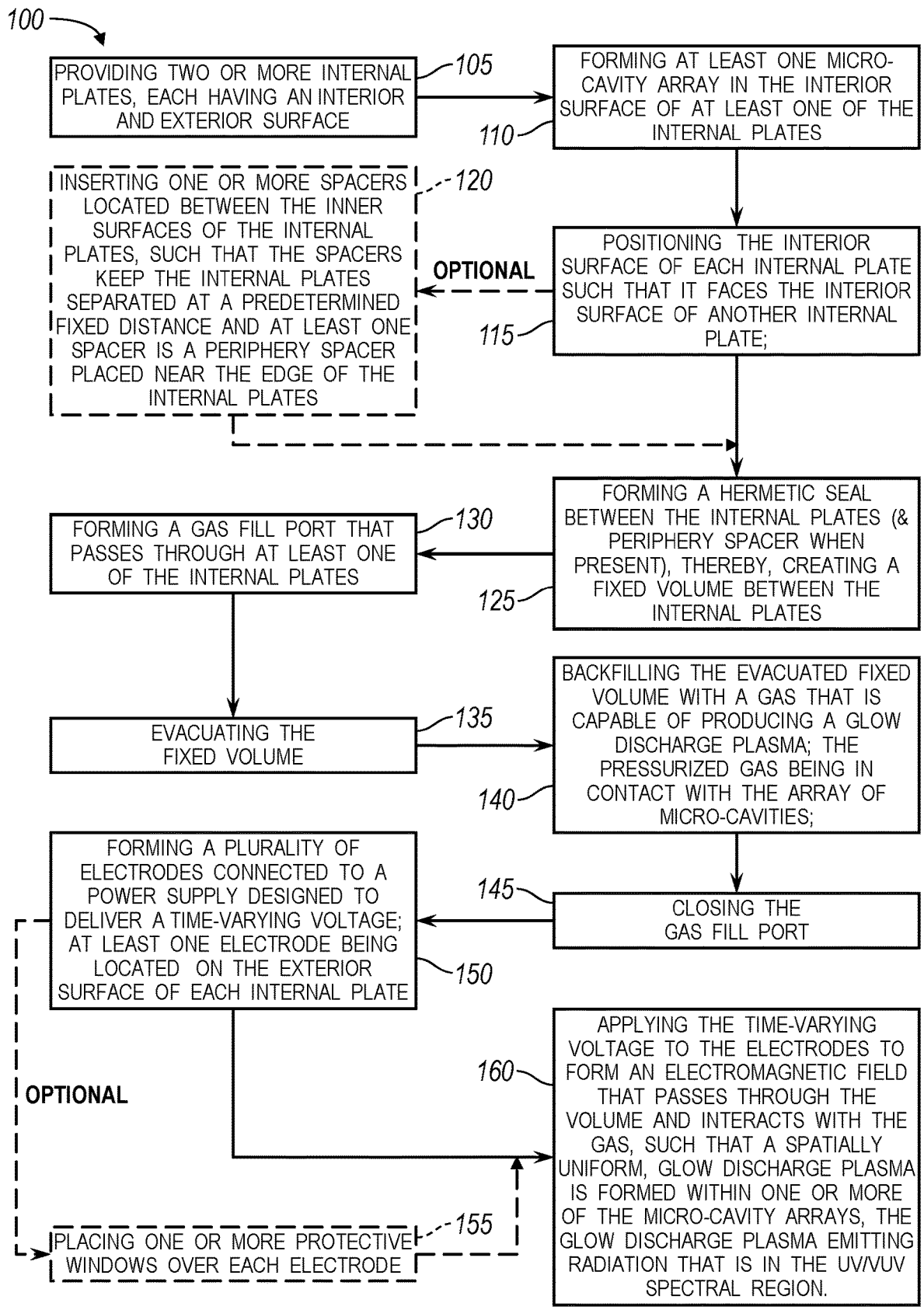
FIG. 11 is a schematic representation of a method for fabricating a plasma lamp according to the teachings of the present disclosure.
Figure 12A:
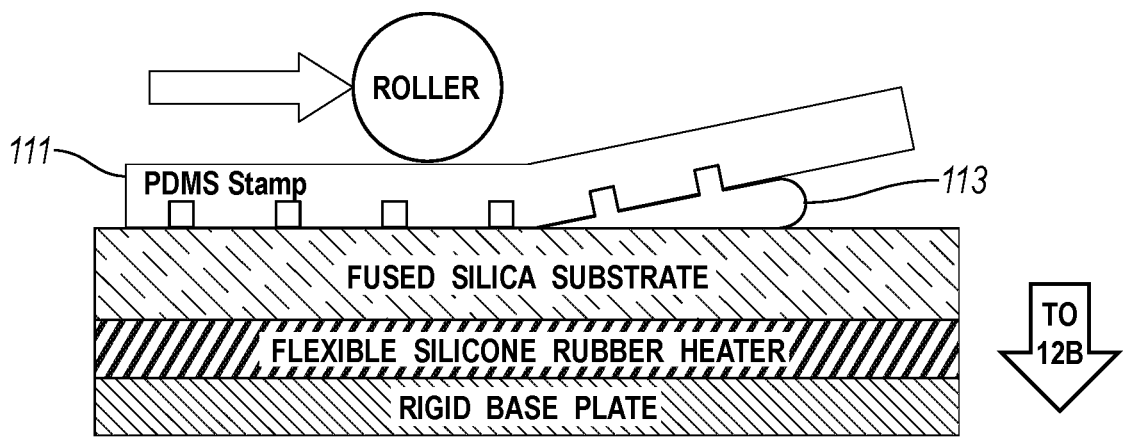
FIGS. 12(A-I) are schematic representations providing further illustration of the various process steps in the method of FIG. 11.
Figure 12B:
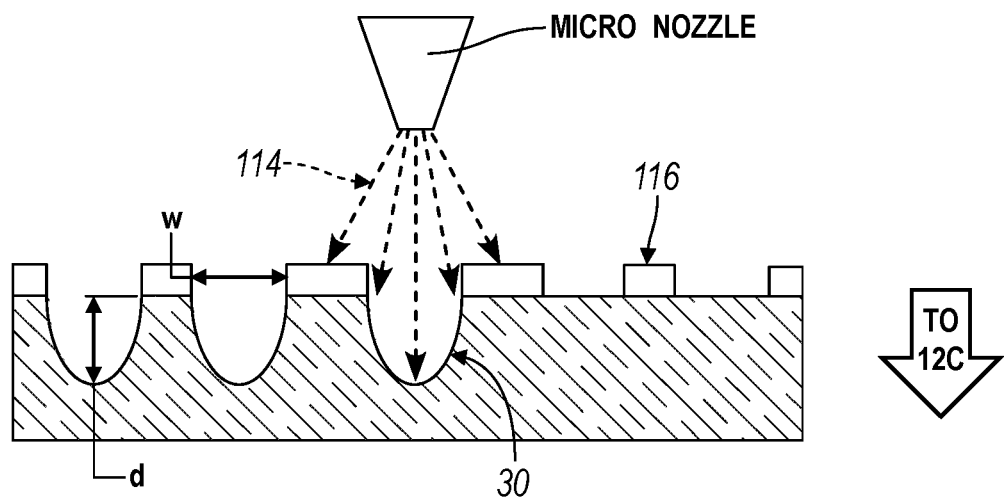
Figure 12C:
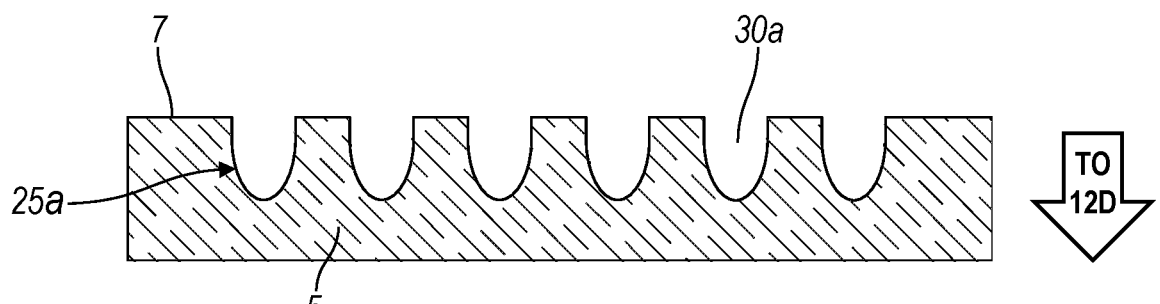
Figure 12D:
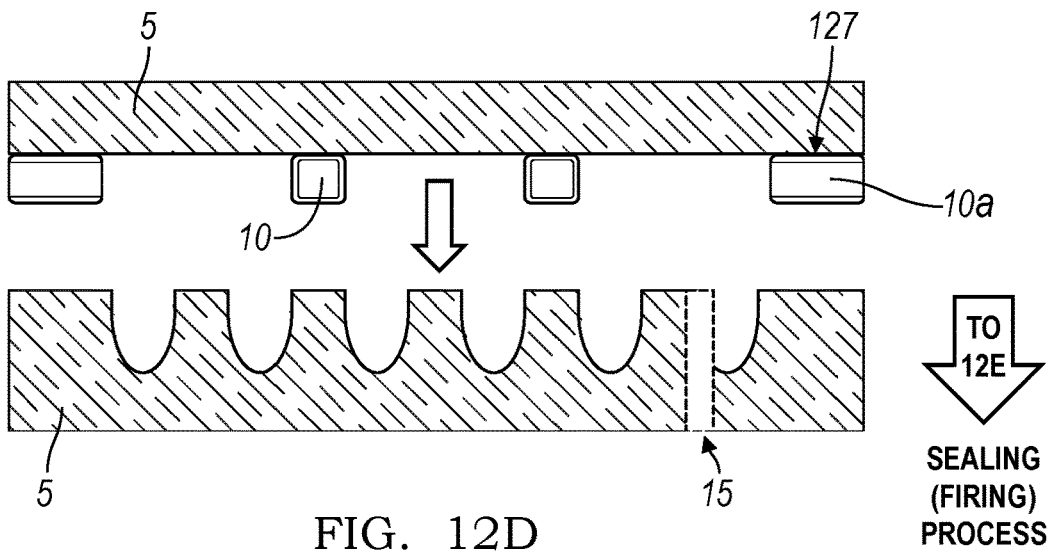
Figure 12E:
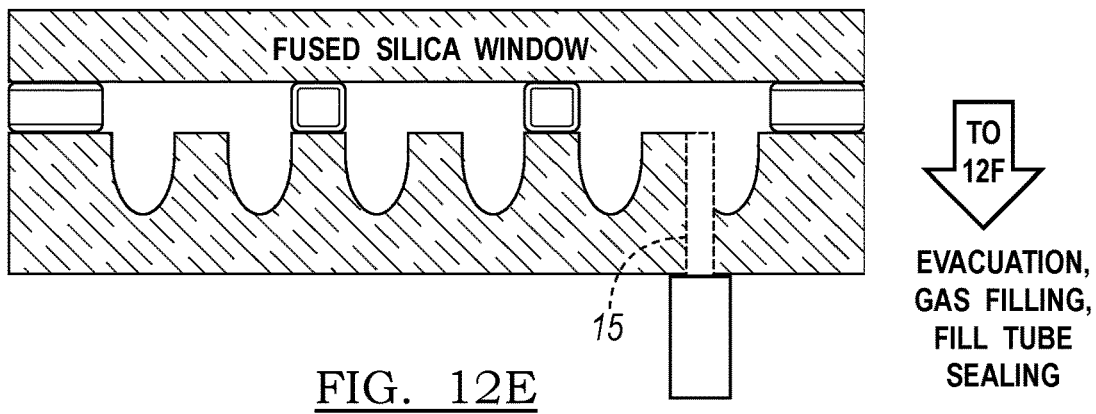
Figure 12F:
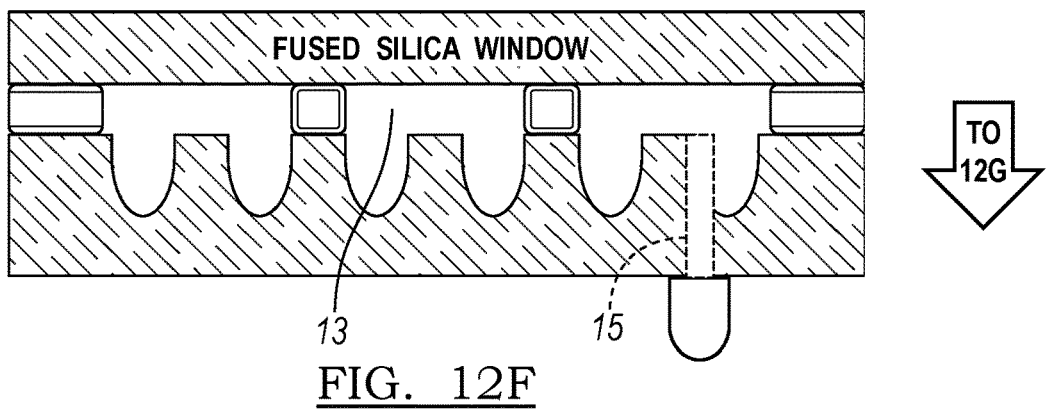
Figure 12G:
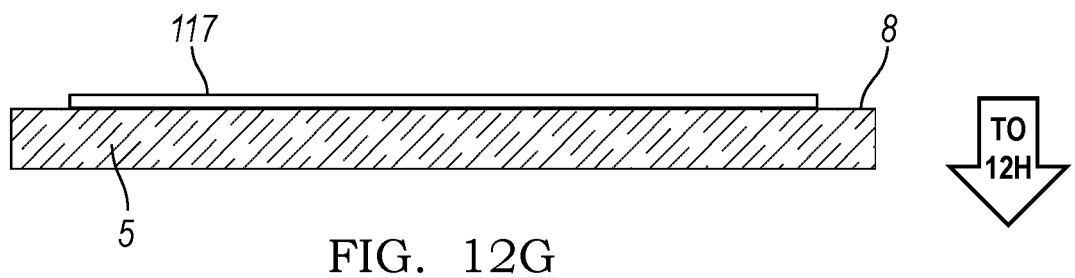
Figure 12H:
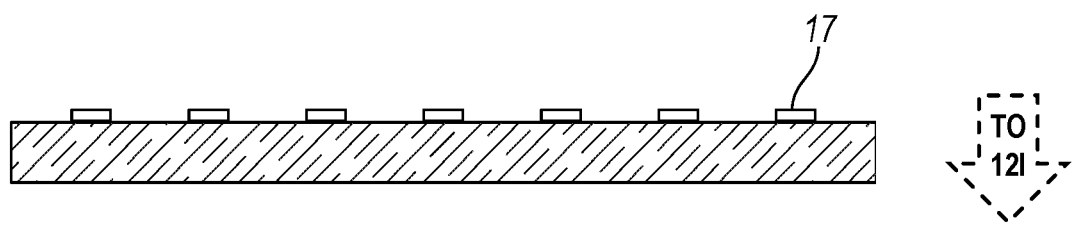
Figure 12I:
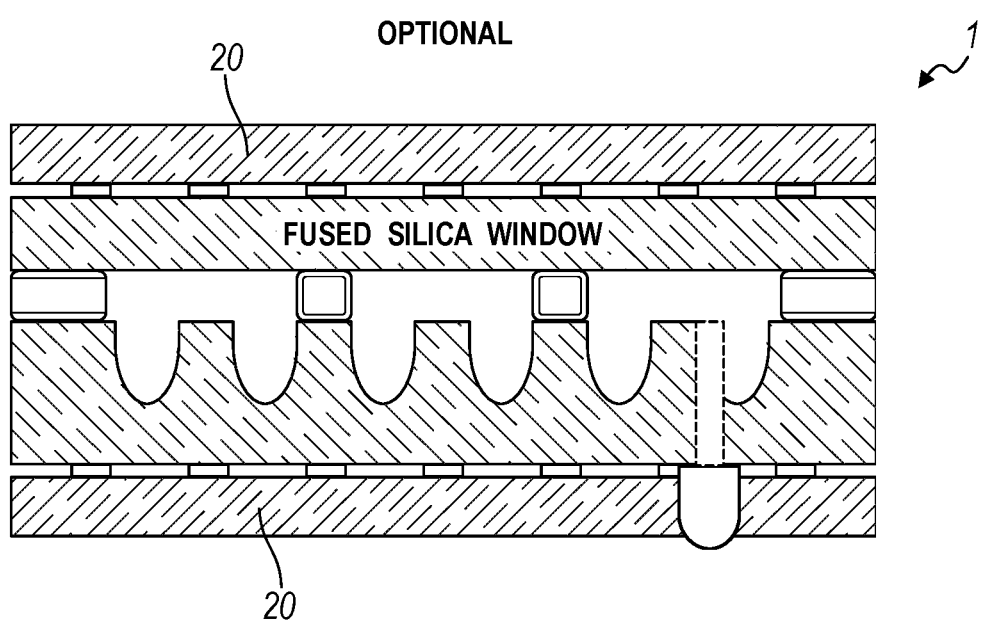
Figure 13A:
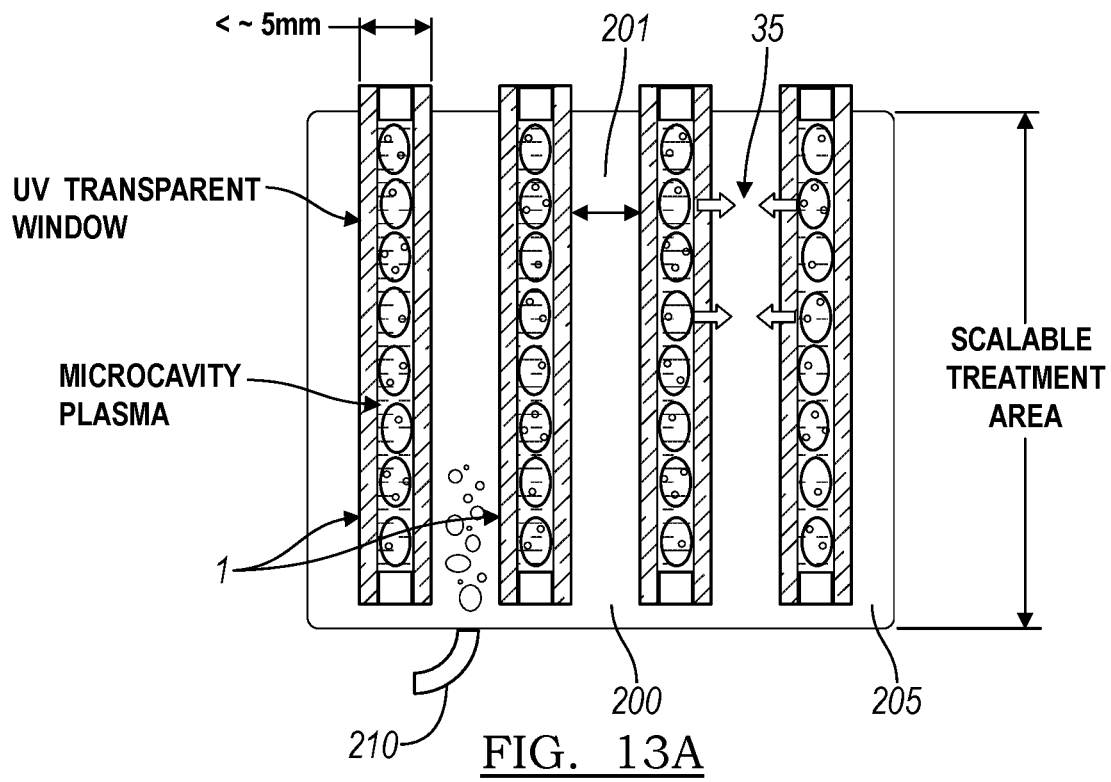
FIG. 13A is a cross-sectional diagram of a product comprising plasma lamps and used for the disinfection of water or the treatment of wastewater.
Figure 13B:
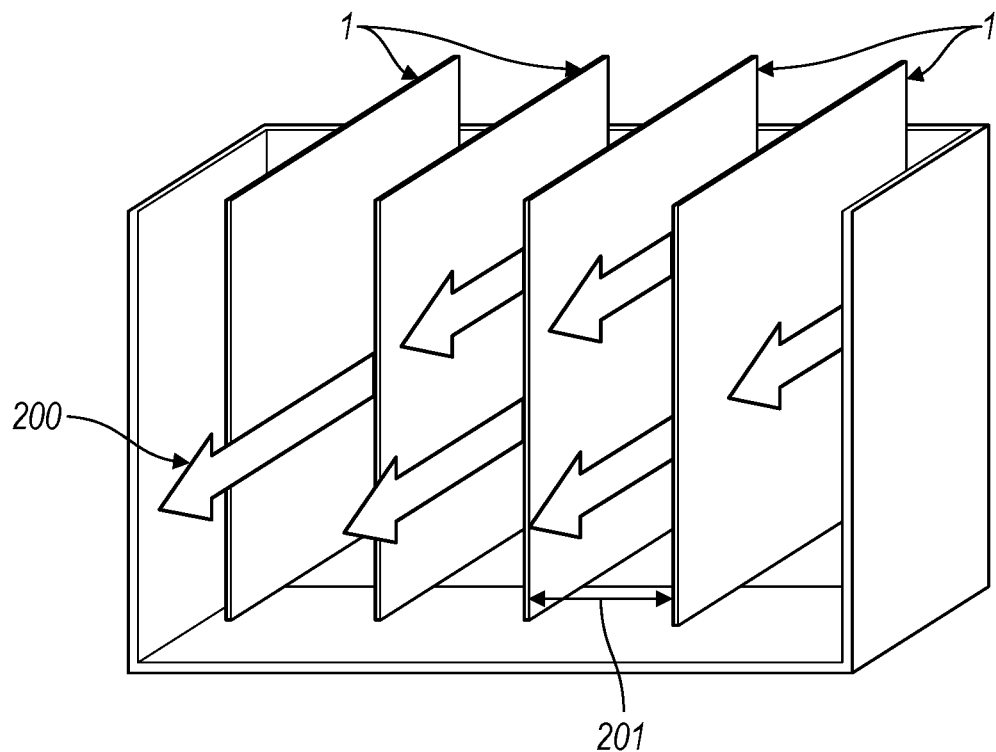
FIG. 13B is a cross-sectional, perspective view of the product of FIG. 14A.
Figure 14A:
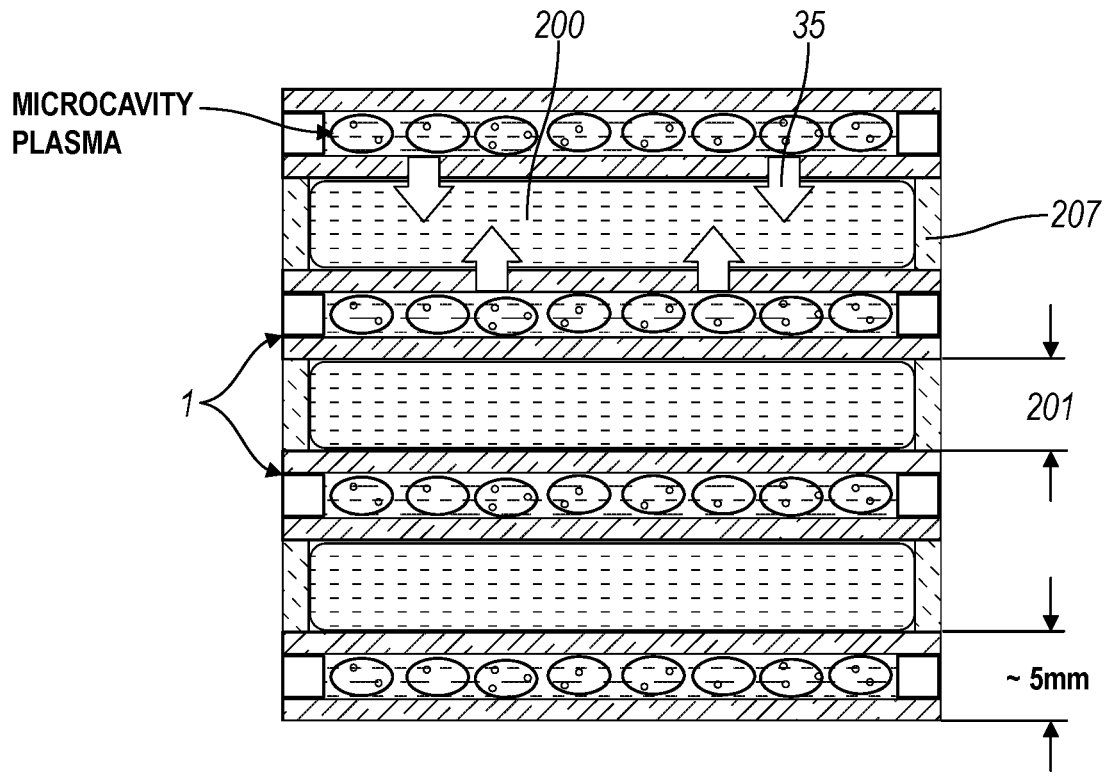
FIGS. 14 (A, B) are cross-sectional diagrams of another system comprising plasma lamps formed according to the teachings of the present disclosure and designed for the treatment of liquid waste.
Figure 14B:
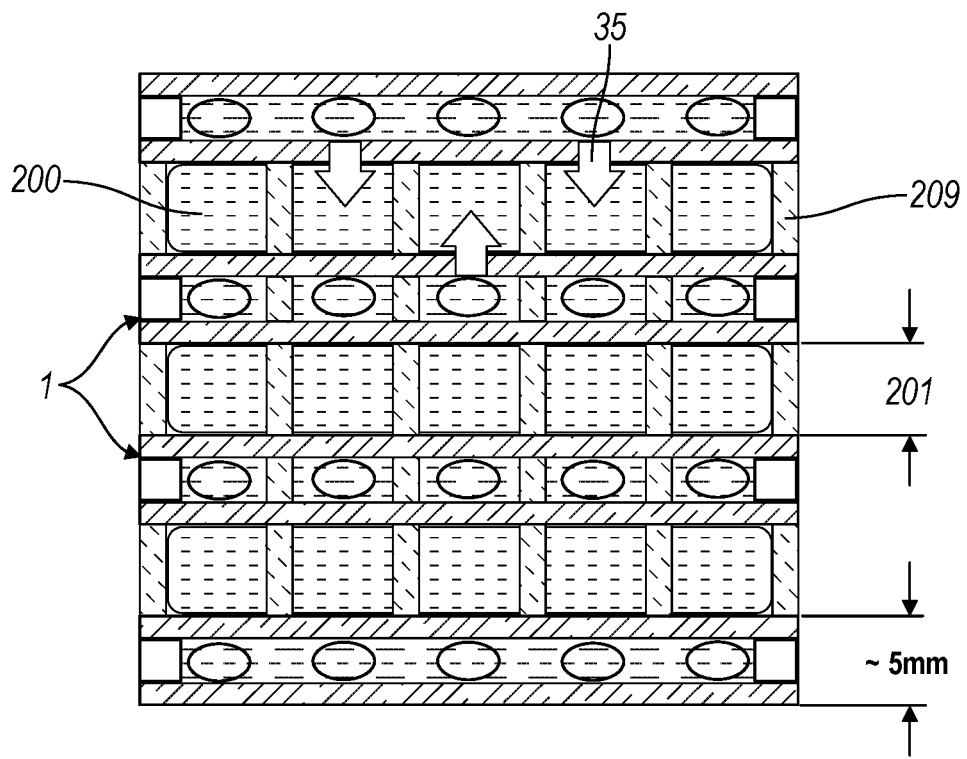

According to another aspect of the present disclosure, a method of forming a plasma lamp having a composite structure is provided. Referring to FIG. 11, the method 100 comprises providing 105 two or more internal plates with each of the internal plates having an interior surface and an exterior surface. At least one microcavity array is formed 110 in the interior surface of at least one of the internal plates. The interior surface of each internal plate is positioned 115 such that it faces the interior surface of another internal plate. Alternatively, the interior surface of each internal plate is parallel to the other. Optionally, one or more spacers may be inserted 120 between the inner surfaces of the internal plates, such that the spacers keep the internal plates separated at a predetermined fixed distance. When used, at least one of the spacers is a periphery spacer placed near the edge of the internal plates. A hermetic seal is formed 125 between the periphery seal and the internal plates, thereby creating a fixed volume between the internal plates. A gas fill port that passes through at least one of the internal plates is formed 130 and the fixed volume is evacuated 135. The evacuated fixed volume is backfilled 140 with a gas (or gas mixture) that is capable of producing a glow discharge. Thus, the gas is in contact with, and fills, the array of microcavities. Once the gas is backfilled 140, the gas fill port is then closed 145, thereby sealing the gas within the plasma lamp. A plurality of electrodes is formed 150 and connected to a power supply designed to deliver a time-varying voltage. At least one electrode is located on the exterior surface of at least one internal plate. Finally, one or more protective windows are placed 155 over at least one electrode; alternatively, over each electrode. Application 160 of the time-varying voltage to the electrodes generates a spatially uniform, glow discharge plasma within one or more of the microcavity arrays, and the glow discharge emits radiation lying in the UV/VUV spectral region.

Referring now to FIG. 12, a specific example of several process steps used to fabricate the plasma lamps of the present disclosure is provided without limitation. Process steps shown in FIGS. 12(*a-c*) entail the production of one or more arrays of microcavities on one face of a flat plate of an optically transmissive material. Although fused silica is specifically indicated in FIG. 12, other materials may also be used, depending on the wavelength(s) of the radiation to be emitted. Exemplary materials that exhibit excellent transmission over most of the VUV region include calcium fluoride, magnesium fluoride, lithium fluoride and sapphire. The positions and transverse dimensions of the microcavities in an array are defined by a lithographic process (illustrated in FIG. 12(*a*)) involving a polydimethylsiloxane (PDMS) stamp 111 and a UV-curable ink 113. The cavities themselves can be formed, without limitation, by a micropowder ablation process (see FIG. 12(*b*)) including the use of micropowders 114 and a high resolution mask 116. The depth (d) and width (w) of each microcavity (as well as, to an extent, the cavity shape) is determined by the time of exposure of the micropowder 114 jet to the surface. An UV-curable ink has been found to be resistant to the micropowder jet and, therefore, can serve as a suitable mask 116 for the cavity fabrication process. Although micropowder ablation is presented in FIG. 12(*b*), the formation of the microcavity arrays by other well-known processes, including laser ablation, drilling and chemical processing, to name a few, are within the scope of the present disclosure. FIG. 12(*c*) shows the completed formation of an array 25*a* of microcavities 30*a* in the interior surface 7 of an internal plate 5.

FIG. 12(*d*) illustrates the insertion of a silica spacer 10 between the two fused silica inner plates 5 for the lamp. The spacer 10, 10*a* may be a single sheet that has been machined so as to define the desired spacer pattern. Alternatively, the spacer 10, 10*a* may be fused silica segments (discs, pellets, cylinders, spheres, etc.) arranged manually or robotically on one of the fused silica windows. Regardless of the configuration of the spacer(s), each portion of the spacer 10, 10*a* can be, when desired, coated on both of its faces with a frit 127 designed for firing at a temperature above 750° C.; alternatively, above 850° C., alternatively, in the range of about 900-950° C. Alternatively, when no spacer or spacers are present, the inner plates 5 then are bonded directly together.

After the two inner plates of the lamp are sealed by a firing process (see FIG. 12(*e*)), a short length of quartz tubing is also sealed to the assembly with glass frit. The interior of the lamp is then evacuated through the gas fill port 15 by a vacuum system, and is subsequently back-filled with the desired gas composition. In order to maximize the purity of the gas or gas mixture in the lamp, it may be necessary to operate the lamp after being filled with gas but before the lamp is sealed. After the lamp is self-heated by the discharge, it can then be evacuated once more and then re-filled. The gas fill tube 15 is then sealed (see FIG. 12(*f*)), thereby trapping the gas 13 in the plasma lamp. When desirable, a small "getter" may also installed within the lamp and fired after the final gas fill is introduced to the lamp, and the lamp is then sealed. The function of the getter is to remove residual impurities (such as water vapor, $O_2$, $N_2$, etc.) that have a deleterious effect on lamp performance. One example of a commercially-available getter is the barium getter marketed worldwide by SAES.

FIGS. 12(*g-i*) illustrate the formation of a metal grid electrode on the outer face of both inner plates (windows) of the lamp. In FIG. 12(*g*), a Cr/Ni layer 117 is deposited onto the external surface 8 of the fused internal silica plates 5. A photolithographic patterning process (FIG. 12(*h*)) may be utilized without limitation to form the Cr/Ni layer into a patterned electrode 17. The assembly process may optionally conclude with sealing two additional quartz windows 20 onto the lamp 1 exterior (see FIG. 12(*i*)). These exterior windows 20 may serve to assist in protecting the electrodes. As noted previously, these additional windows can be discarded if the lamp power they absorb (owing to color center formation) is objectionable. Thus, when desirable, the additional or protective windows may be absent or not used in forming the plasma lamp.

The following specific examples are given to illustrate the use of the plasma lamps of the present disclosure, as well as the products formed therefrom, and should not be construed as limiting the scope of the disclosure. Those skilled-in-the-art, in light of the present disclosure, will appreciate that many changes can be made in the specific embodiments which are disclosed herein and still obtain alike or similar results without departing from, or exceeding, the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

Referring now to FIGS. 13-17, the use of the plasma lamps 5 prepared according to the method described above, and as further defined herein, are highlighted in several applications, without limitation. One such application as described in FIGS. 13*a*-14*b* includes, but is not limited to, the disinfection and treatment of water. Owing to the planar nature of the VUV-emitting lamps 1, multiple lamps 1 can be positioned so as to be parallel, thereby allowing water 200 to pass between the planar lamps 1 in a channel 201. One skilled in the art will understand that if or when desired, the plasma lamp may comprise a curved surface. UV/VUV radiation 35 emitted from the plasma generated in the lamps 1 destroys bacteria and pathogens in the water 200. This UV/VUV radiation 35 is also capable of effecting photochemical reactions that will dissociate (break apart) undesirable molecules in waste water 200 such as aromatic hydrocarbons. Because the lamps are flat, the distance between the lamps is a constant which stands in contrast to cylindrical lamps placed in any geometrical arrangement in which their axes are parallel. The distance between the lamps 1 may range from about 0.5 mm to about 50 mm; alternatively, between about 0.5 mm and 10 mm. Optionally, the plurality of plasma lamps may be located within a light reflective bath 205, or a flow cell 207 that may be bonded to the lamps 1 and/or form a channel array 209. In addition, nitrogen or another relatively inert gas 210 may be bubbled through the flowing water 200.

Figure 15A:
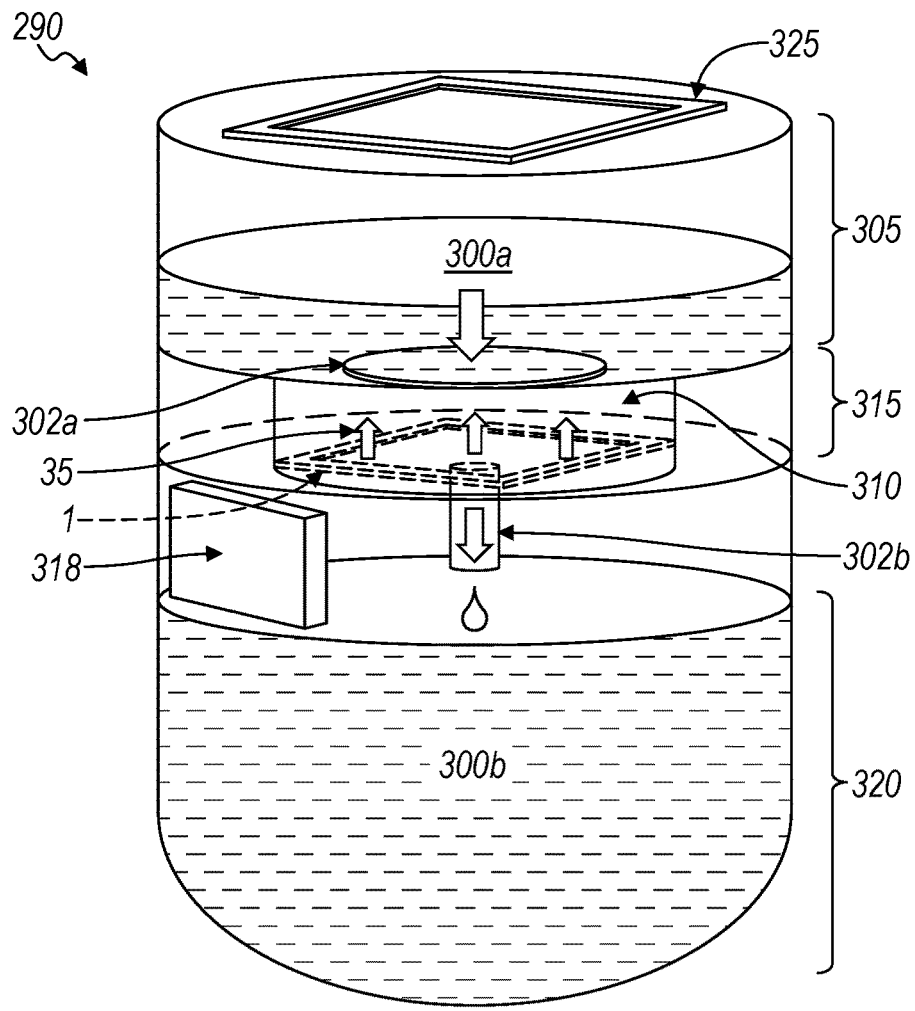
FIG. 15A is a cross-sectional, perspective view of a compact system designed for disinfecting and/or treating water.
Figure 15B:
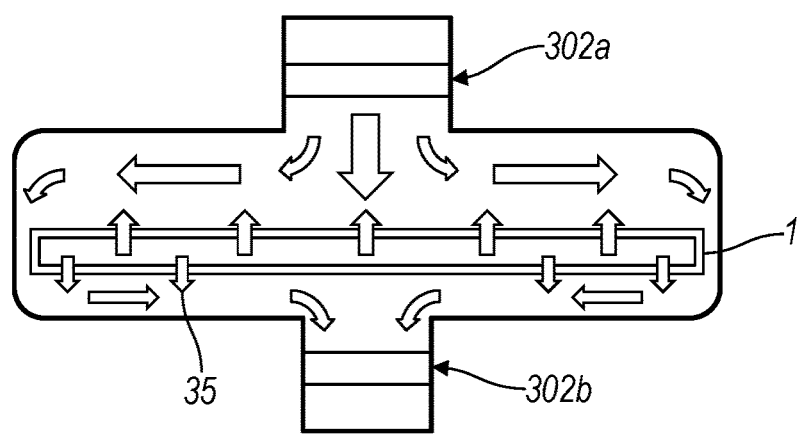
FIG. 15B is an enlarged cross-sectional view of the plasma lamp component in the compact system of FIG. 16A.

In FIG. 15, a diagram of a miniature water disinfection system 290, designed to be lightweight and portable, is illustrated. Although the system 290 may be any size desired, a size that is both lightweight and portable may have a diameter that is in the range of about 10 to 12 cm. This water disinfection system 290 comprises a pretreatment compartment 305 for field or waste water 300a, a pre-filter 302a, a water treatment compartment 310 that comprises at least one plasma lamp 1 and a water treatment chamber 315, wherein UV/VUV radiation 35 arising from the plasma lamp 1 interacts with the waste water 300a, thereby treating (disinfecting, reducing organic molecule concentration, etc.) the waste water 300a. The plasma lamp can be powered by a power circuit and a battery pack 318, rendering the system completely portable. The treated water 300b passes through a second filter 302b and into a purified water reservoir 320. The pre-treatment compartment 305 may optionally comprise a compact solar panel or battery compartment 325, when desirable.

Figure 16:
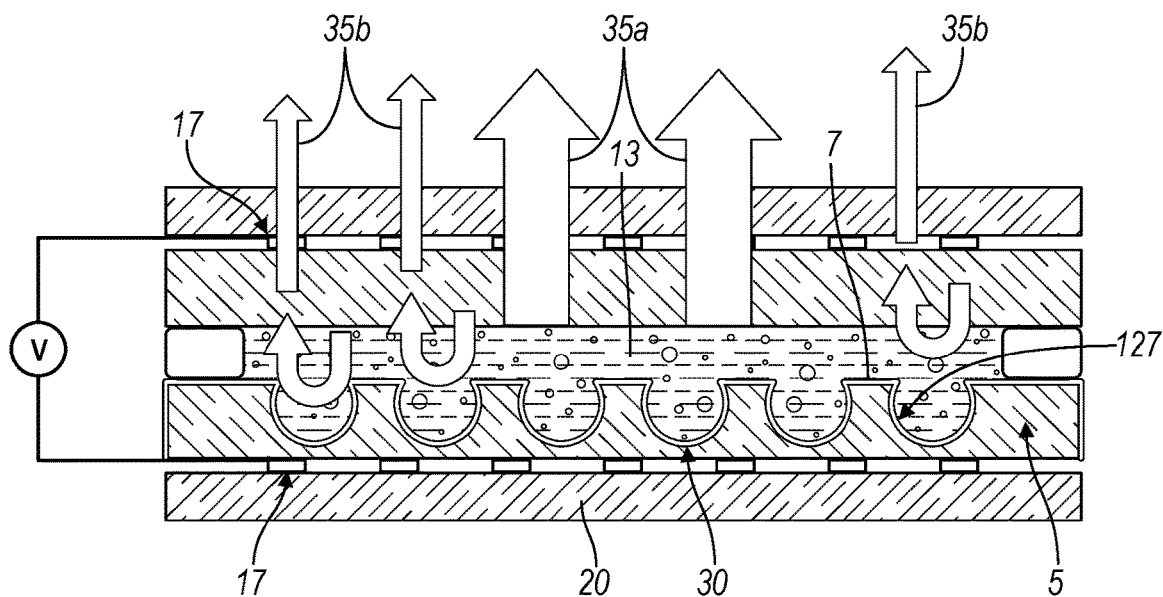
FIG. 16 is a cross-sectional view of a plasma lamp capable of providing radiation simultaneously in two or more VUV/UV/Visible wavelength regions.

FIG. 16 is a diagram describing another aspect of the present disclosure which is capable of producing UV/VUV radiation in two or more spectral regions 35a, 35b. The flat geometry of the plasma lamp 1 surface can be segmented, in order for different regions of the lamp to be devoted to the generation of distinct wavelengths. A UV conversion phosphor material 127 may be coated onto a portion of the interior surface 7 of an internal plate 5 in order to cause a change in the wavelength of the emitted UV/VUV radiation 35a, 35b. The availability, from a single, compact lamp, of UV and/or VUV photons in two or more separate regions of the spectrum is of considerable value for applications including disinfection (because different pathogens are deactivated preferentially at different wavelengths) and biomedical diagnostics in which chromophore "tagged" biological molecules emit visible fluorescence in response to the absorption of UV or VUV photons. It should be noted that attempting to coat different regions on the interior surface of a cylindrical lamp with different phosphors is fraught with difficulty, but doing so on the interior surface of a flat lamp prior to lamp assembly is comparatively straightforward.

Figure 17:
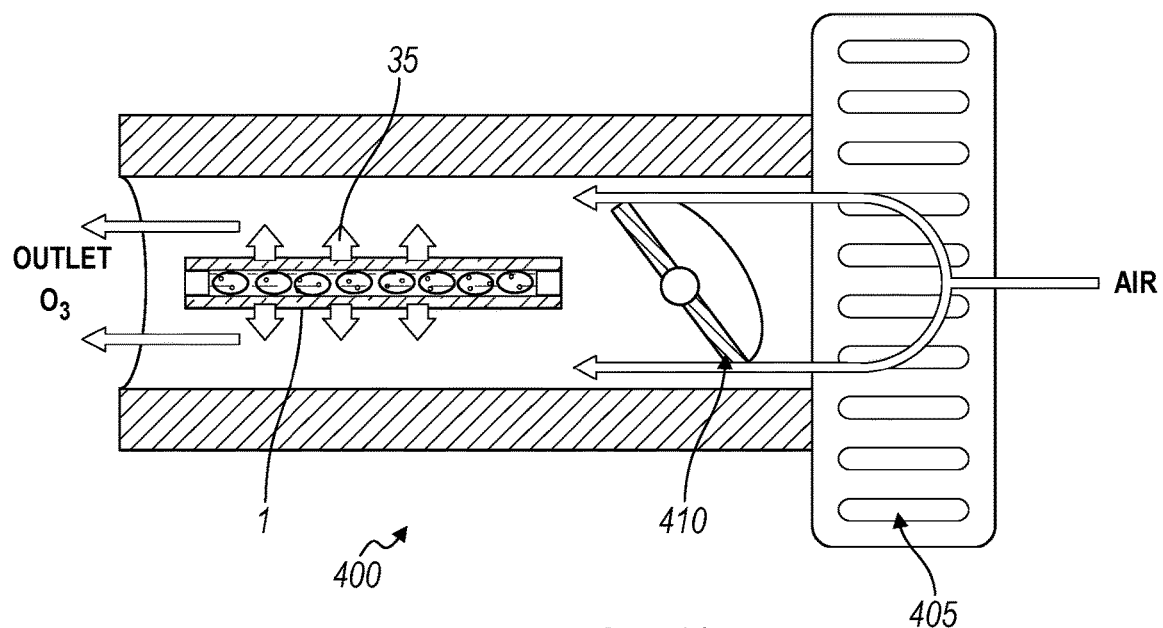
FIG. 17 is a schematic diagram of a plasma lamp designed to generate O3 (ozone) in the air intake of an internal combustion engine such as that in an automobile.

In FIG. 17, a system 400 for generating ozone (O3) within the air intake of an automobile engine is illustrated. Due to the high efficiency and compact nature of plasma lamps 1 of the present disclosure, it is now practical to situate a small $Xe_2^*$ (172 nm) emitting lamp 1 in the automobile engine. The exposure of 172 nm radiation 35 to conventional air produces ozone efficiently. Stated another way, it is known that the oxygen in air absorbs strongly at the 172 nm wavelength of the Xe dimer lamp. When oxygen absorbs a 172 nm photon, the molecule is dissociated into two free oxygen atoms. The interaction of these free atoms with oxygen molecules produces ozone. Because ozone is known to increase the gas mileage of automobiles, the introduction of an efficient 172 nm lamp into the air-intake 405, located immediately prior to the combustion process and downstream of the throttle valve 410, is expected to provide an economical system for increasing significantly the mileage of all automobiles. A similar system is expected to also be effective in improving the mileage of trucks, busses, and all vehicles (tractors, aircraft, etc.) and products (mowers, trimmers, etc.) that require an internal combustion engine. For larger engines in which the air flow is higher, an array of lamps or a single larger lamp may be required. It should also be mentioned that ozone is not only believed to increase the mileage of automobiles, trucks, etc. because it improves the combustion process, it also increases the power produced by the engine for a given amount of fuel consumed per engine cycle. Therefore, the increased power produced by the engine is expected to be of particular value for aircraft (propeller-driven as well as jets) and, for a given amount of horsepower from a conventional internal combustion engine, this benefit of ozone-assisted combustion will reduce fuel consumption further.

Within this specification, embodiments have been described in a manner which enables a clear and concise specification to be written, but it is intended, and will be appreciated by artisans, that embodiments may be variously combined or separated without departing from the invention. For example, it will be appreciated that all preferred features described herein are applicable to all aspects of the invention described herein.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A product that includes at least one UV/VUV-emitting plasma lamp; the plasma lamp comprising:

two or more internal plates, each internal plate having an interior surface and an exterior surface; the internal surface of each internal plate being positioned approximately parallel to and separated by a predetermined distance from the internal surface of another internal plate, such that a fixed volume is formed between the internal plates;

at least one array of microcavities formed in the interior surface of at least one of the internal plates, the microcavities in the at least one array comprising a geometric shape having a predetermined primary spatial width that is in the range of about 3 μm to about 5,000 μm and/or a predetermined spatial depth that is in the range of about 1 μm to about 1,000 μm;

a gas or mixture of gases in which a glow discharge (plasma) is produced; the gas occupying the fixed volume between the internal plates and being in contact with the at least one array of microcavities; and a plurality of electrodes connected to a power supply designed to deliver a time-varying voltage;

wherein the time-varying voltage interacts with the gas, such that a spatially uniform, glow discharge (plasma)

is formed both within the microcavities and the fixed volume between the internal plates, the glow discharge (plasma) producing radiation that is predominantly in the UV/VUV spectral region with at least a portion of the radiation being emitted from the plasma lamp.

2. The product according to claim 1, wherein the predetermined distance is defined by one or more spacers located between the interior surfaces of the internal plates, wherein at least one spacer is a periphery spacer placed near the edge of the internal plates, the periphery spacer forming a hermetic seal with the internal plates.

3. The product according to claim 2, wherein the spacers are either part of a monolithic structure that exhibits a predetermined spacer pattern or discrete structures having the shape of a disc, a sphere, a pellet, a cylinder, a cube, or a mixture thereof.

4. The product according to claim 1, wherein one or more of the internal plates are individually selected to comprise a UV/VUV radiation transmissive material such as fused silica, quartz, sapphire, or magnesium fluoride, and at least one of the plurality of electrodes exhibits a transparency to UV/VUV radiation of 90% or more.

5. The product according to claim 4, wherein at least one of the plurality of electrodes is located on the exterior surface of at least one of the internal plates.

6. The product according to claim 5, wherein one or more protective windows in the form of a transparent plate or a coating are placed on the opposite side of the at least one electrode on the exterior surface in order to provide environmental and safety protection thereto.

7. The product according to claim 1, wherein the spatial depth is between about 5 μm to about 600 μm and/or the spatial width is between about 5 μm to about 1,500 μm.

8. The product according to claim 1, wherein the geometric shape of the microcavities is one selected from the group of a cylinder, hemisphere, a half-cylinder, an ellipsoid, a truncated cone, a paraboloid, a truncated paraboloid, and a cube.

9. The product according to claim 1, wherein the plasma lamp has a thickness that is about 6 mm or less; the plasma lamp being either planar or comprising a curved surface.

10. The product according to claim 1, wherein the gas comprises one or more noble gases, one or more halogen-containing molecular gases, or a mixture of at least one halogen-containing gas with the one or more noble gases.

11. The product according to claim 10, wherein the glow discharge (plasma) produces molecules from the gas that emit UV/VUV radiation having a peak wavelength; the molecules (and their associated peak wavelengths) being selected from the group of NeF* (108 nm), $Ar_2$* (126 nm), $Kr_2$* (146 nm), $F_2$* (158 nm), ArBr* (165 nm), $Xe_2$* (172 nm), ArCl* (175 nm), KrI* (190 nm), ArF* (193 nm), KrBr* (207 nm), KrCl* (222 nm), KrF* (248 nm), XeI* (254 nm), $Cl_2$* (258 nm), XeBr* (282 nm), $Br_2$* (289 nm), ArD* (290-300 nm), XeCl* (308 nm), $I_2$* (342 nm), and XeF* (351, 353 nm).

12. The product according to claim 1, wherein the plasma lamp further comprises a planar reflector or a reflecting surface positioned so as to increase the power of the UV/VUV radiation emitted from the lamp.

13. The product according to claim 12, wherein the planar reflector comprises a diffractive structure, such that at least one preferred wavelength is reflected preferentially by the planar reflector.

14. The product according to claim 1, wherein the plasma lamp emits an average output intensity that is greater than 200 mW/cm$^2$ and a peak power that is greater than approximately 1 kW when the gas is xenon (or a Ne/Xe or Ar/Xe mixture) and the UV/VUV radiation is emitted predominantly from the $Xe_2$* excimer molecule at a peak wavelength of about 172 nm.

15. The product according to claim 1, wherein the plasma lamp further comprises one or more UV/VUV-to-UV or UV/VUV-to-visible conversion phosphor materials located on the interior surface of at least a portion of at least one of the internal plates.

16. The product according to claim 1, wherein the plasma lamp comprises at least two different arrays of microcavities, such that the microcavities in the different arrays exhibit a different geometric shape, primary spatial width, spatial depth, or a combination thereof.

17. The product according to claim 16, wherein the different arrays of microcavities are spatially separated on the interior surface of the internal plate, or interlaced or interwoven, such that the microcavities in one array are alternated or staggered with the microcavities of another array.

18. The product according to claim 16, wherein the product produces radiation simultaneously in two or more wavelength ranges within the UV/VUV spectral region.

19. The product according to claim 1, wherein the product is used to disinfect potable water; disinfect medical devices, clothing, or surfaces; deactivate biological pathogens; treat waste water; desorb contaminants or hydrocarbons from an internal surface of a chamber or the surface of a component or tool used in a cleanroom or surgical environment; generate ozone near the air intake of an internal combustion engine or a jet engine; or cure a coating composition after it has been applied to a surface of a substrate.

20. The product according to claim 1, wherein the product comprises a plurality of plasma lamps that are tiled in order to realize an emitting surface that produces an average power between 10 W and 10 kW in the UV/VUV spectral range.

21. A product that includes at least one plasma lamp; the plasma lamp comprising:
  two or more internal plates with one or more of the internal plates being individually selected to comprise a UV/VUV radiation transmissive material; each internal plate having an interior surface and an exterior surface; the internal surface of each internal plate being positioned approximately parallel to and separated by a predetermined distance from the internal surface of another internal plate, such that a fixed volume is formed between the internal plates; the predetermined distance being defined by one or more spacers located between the interior surfaces of the internal plates, wherein at least one spacer is a periphery spacer placed near the edge of the internal plates, the periphery spacer forming a hermetic seal with the internal plates;
  one or more UV conversion phosphor materials located on the interior surface of at least a portion of at least one of the internal plates;
  at least one array of microcavities formed in the interior surface of at least one of the internal plates, the microcavities in the at least one array comprising a geometric shape having a predetermined primary spatial width that is in the range of about 5 μm to about 1,500 μm and/or a predetermined spatial depth that is in the range of about 5 μm to about 600 μm;
  a gas in which a glow discharge (plasma) is produced, the gas comprising one or more noble gases, one or more halogen-containing molecular gases, or a mixture of at least one halogen-containing gas with the one or more noble gases; the gas occupying the fixed volume between the internal plates and being in contact with the at least one array of microcavities; and a plurality of electrodes connected to a power supply designed to deliver a time-varying voltage; at least one of the plurality of electrodes exhibits a transparency to UV/VUV radiation of 90% or more;

wherein the time-varying voltage interacts with the gas, such that a spatially uniform, glow discharge (plasma) is formed both within the microcavities and the fixed volume between the internal plates, the glow discharge (plasma) producing radiation that is in the UV/VUV spectral region with at least a portion of the radiation being emitted from the plasma lamp.

22. The product according to claim 21, wherein the plasma lamp comprises at least two different arrays of microcavities, such that the microcavities in the different arrays exhibit a different geometric shape, primary spatial width, spatial depth, or a combination thereof;

wherein the different arrays of microcavities are spatially separated on the interior surface of the internal plate, or interlaced or interwoven, such that the microcavities in one array are alternated or staggered with the microcavities of another array.

* * * * *